(12) United States Patent
Brochet et al.

(10) Patent No.: US 12,054,692 B2
(45) Date of Patent: Aug. 6, 2024

(54) MICROWAVE ASSISTED EXTRACTION OF ESSENTIAL OILS FROM PLANT BIOMASS

(71) Applicant: FIRMENICH SA, Satigny (CH)

(72) Inventors: Xavier Brochet, Grasse (FR); Philippe Pineau, Grasse (FR)

(73) Assignee: FIRMENICH SA, Satigny (CH)

( * ) Notice: Subject to any disclaimer, the term of this patent is extended or adjusted under 35 U.S.C. 154(b) by 609 days.

(21) Appl. No.: 16/642,592

(22) PCT Filed: Aug. 29, 2018

(86) PCT No.: PCT/EP2018/073242
§ 371 (c)(1),
(2) Date: Feb. 27, 2020

(87) PCT Pub. No.: WO2019/043058
PCT Pub. Date: Mar. 7, 2019

(65) Prior Publication Data
US 2020/0347318 A1 Nov. 5, 2020

(30) Foreign Application Priority Data
Oct. 25, 2017 (EP) .................................... 17198347

(51) Int. Cl.
| C11B 9/02 | (2006.01) |
| A61K 8/92 | (2006.01) |
| A61K 8/9789 | (2017.01) |
| A61K 8/9794 | (2017.01) |
| A61Q 5/00 | (2006.01) |
| A61Q 5/02 | (2006.01) |
| A61Q 13/00 | (2006.01) |
| A61Q 19/00 | (2006.01) |
| B01D 11/02 | (2006.01) |
| C11B 9/00 | (2006.01) |

(52) U.S. Cl.
CPC .............. *C11B 9/027* (2013.01); *A61K 8/922* (2013.01); *A61K 8/9789* (2017.08); *A61K 8/9794* (2017.08); *A61Q 5/00* (2013.01); *A61Q 5/02* (2013.01); *A61Q 13/00* (2013.01); *A61Q 19/00* (2013.01); *B01D 11/0211* (2013.01); *B01D 11/023* (2013.01); *C11B 9/0015* (2013.01); *C11B 9/0019* (2013.01); *C11B 9/003* (2013.01); *C11B 9/0034* (2013.01); *C11B 9/0046* (2013.01); *C11B 9/0049* (2013.01); *C11B 9/0061* (2013.01); *C11B 9/0076* (2013.01); *C11B 9/008* (2013.01); *C11B 9/0092* (2013.01); *C11B 9/0096* (2013.01)

(58) Field of Classification Search
CPC .... A61K 8/9794; A61K 8/9789; A61K 8/922; A61Q 5/00; A61Q 5/02; A61Q 13/00; A61Q 19/00
See application file for complete search history.

(56) References Cited

U.S. PATENT DOCUMENTS

| 5,338,557 A | * | 8/1994 | Pare | ........................ | C11B 9/025 426/430 |
| 9,005,336 B2 | | 4/2015 | Toshihiko et al. | | |

FOREIGN PATENT DOCUMENTS

| CN | 105219526 A | 1/2016 |
| EP | 1618798 A1 | 1/2006 |
| EP | 1955749 A1 | 8/2008 |
| FR | 3003181 A1 | 9/2014 |
| JP | H08512337 A | 12/1996 |
| WO | 2010098440 A1 | 9/2010 |

OTHER PUBLICATIONS

Chemat F. et al. "Chapter 3: Microwave-Assisted Extraction of Essential Oils and Aromas" In: Microwave-Assisted Extraction for Bioactive Compounds: Theory and Practice, Jun. 26, 2014, pp. 53-66. (Year: 2014).*
Hackleman et al. ("Microwave Extraction of Essential Oil from Peppermint-Field Trial," article, Oregon State University, Corvallis, Oregon; 2012). (Year: 2012).*
Chemat et al., ("Microwave-Assisted Extraction of Essential Oils and Aromas" Chapter 3 in Microwave-Assisted Extraction for Bioactive Compounds: Theory and Practice, Jun. 26, 2014, pp. 53-68). (Year: 2014).*
1. Ito Koichi et al. (JP 2007245095 A, using Eng. Trans. on PE2E). (Year: 2007).*
Racoti et al (Journal of Essential Oil Research, Aug. 2017, pp. 1-13) (Year: 2017).*
Racoti et al (Journal of Essential Oil Research, Aug. 2017, pp. 1-13; Abstract with date) (Year: 2017).*
Foley (COMSOL Blog, Sep. 3, 2013, https://www.comsol.com/blogs/why-does-a-microwave-heat-food-unevenly/) (Year: 2013).*
International Search Report and Written Opinion of corresponding PCT/EP2018/073242, mailed Sep. 1, 2019, 14 pages.
Chemat F. et al. "Chapter 3: Microwave-Assited Extraction of Essential Oils and Aromas" In: Microwave-Assisted Extraction for Bioactive Compounds: Theory and Practice, Jun. 26, 2014, pp. 53-66.
Vinatoru M. et al. "Ultrasonically assisted extraction (UAE) and microwave assisted extraction (MAE) of functional compounds from plant materials", Trac Trends in Analytical Chemistry, vol. 97, Sep. 14, 2017, pp. 159-178.
Compound summary Jasmone, Pubchem by National Library of Medicine, National Center for Biotechnology Information.
Anne Orav et al., "Effect of storage on the essential oil composition of *Piper nigrum* L. fruits of different ripening states" J. Agric. Food Chem., May 5, 2004, vol. 52, No. 9, pp. 2582-2586, doi: 10.1021/jf030635s.

(Continued)

*Primary Examiner* — Mark V Stevens
(74) *Attorney, Agent, or Firm* — Armstrong Teasdale LLP

(57) ABSTRACT

Described herein are essential oils, extracts, apparatus and methods for the extraction of the essential oils and extracts from plant biomass using microwaves.

7 Claims, 3 Drawing Sheets

(56) References Cited

OTHER PUBLICATIONS

Twahira Begum et al., "Essential Oil Composition of Different Accessions of Ginger Collected from Northeast Region of India", J. Essential Oil Bearing Plants, 2018, vol. 21, No. 6, pp. 1475-1486, doi: 10.1080/0972060X.2018.1559104.

Bianca Zierer et al., "Aroma-Active Compounds in Bartlett Pears and Their Changes during the Manufacturing Process of Bartlett Pear Brandy", J. Agric. Food Chem. 2016, vol. 64, No. 50, pp. 9519522, doi: 10.1021/acs.jafc.6b04612.

Gloria Inés Puerta Quintero, "Composición química de una taza de café", Avances Técnicos Cenicafé, Fondo Nacional de Café, Colombia, Dec. 2011, No. 414, pp. 1-12, ISSN-0120-0178.

* cited by examiner

MICROWAVE ASSISTED EXTRACTION OF ESSENTIAL OILS FROM PLANT BIOMASS

CROSS-REFERENCE TO RELATED APPLICATIONS

The present application is a U.S. National Phase Application of PCT/EP2018/073242, filed Aug. 29, 2018, which claims the benefit of priority to U.S. Provisional Patent Application Ser. No. 62/552,593, filed on Aug. 31, 2017, and European Patent Application Serial No. 17198347.1, filed on Oct. 25, 2017, the entire contents of which are hereby incorporated by reference in their entirety.

FIELD OF THE INVENTION

The present disclosure relates to essential oils, extracts, apparatus and methods for the extraction of the essential oils and extracts from plant biomass using microwaves.

BACKGROUND

Microwave assisted extraction of essential oils from plant biomass has had limited commercial development. Problems encountered in scaling up microwave assisted extraction methods up to an industrial scale include, for example, consistently obtaining essential oils from large quantities of plant biomass. Accordingly, there is a need for microwave assisted extraction methods at an industrial scale.

SUMMARY

One aspect presented herein provides a method,
wherein the method obtains an extract from plant biomass,
wherein the method comprises the steps of:
  a. obtaining the plant biomass;
  b. placing the plant biomass onto a conveyor belt, having a length, and introducing the plant biomass into a vessel having length, via the conveyor belt, wherein the plant biomass is introduced into the vessel by moving the conveyer belt at a first velocity, and
  wherein the plant biomass is introduced into the vessel at a rate;
  c. subjecting the plant biomass to microwave energy, of a first intensity, for a time sufficient to heat the biomass to a temperature to vaporize water within the biomass, thereby producing a distillate; and
  d. collecting the distillate.

In one aspect, the extract comprises an essential oil.
In one aspect, the time sufficient to heat the biomass to a temperature to vaporize water is controlled by the first velocity of the conveyer belt, the length of the conveyer belt, the first intensity of the microwave energy, the length of the vessel, the temperature within the vessel, or any combination thereof.
In one aspect, the plant biomass is introduced into the vessel at a rate from 4 to 12 Kg of plant biomass per hour.
In one aspect, the first intensity of the microwave energy is from 0.2 to 0.6 KWH per Kg of plant biomass.
In one aspect, the temperature of the inside of the vessel is from 40 to 100 degrees Celsius.
In one aspect, the collected distillate comprises from 200 to 3000 ppm essential oils.
In one aspect, the collected distillate is further processed to obtain the essential oils.

One aspect presented herein provides an essential oil extracted from at least one plant of the *Jasminium* species, wherein the essential oil comprises at least 7% w/w (z)-jasmone.
In one aspect, the essential oil comprises from 7 to 10% w/w (z)-jasmone.
In one aspect, the at least one plant of the *Jasminium* species is selected from the group consisting of *Jasminium grandiflorum* and *Jasminium sambac*.
In one aspect, the essential oil further comprises at least 5% w/w (±)-3,7-Dimethyl-1,6-octadien-3-ol.
In one aspect, the essential oil further comprises at least 16% w/w (±)-3,7-Dimethyl-1,6-octadien-3-ol.
In one aspect, the essential oil further comprises at least 20% w/w benzyl acetate.
In one aspect, the essential oil further comprises no more than 6% w/w benzyl benzoate.

One aspect presented herein provides an essential oil extracted from *Piper nigrum*, wherein the essential oil comprises at least 7% w/w sabinine.
In one aspect, the essential oil comprises from 9 to 15% w/w sabinine.
In one aspect, the essential oil further comprises from 12 to 16% w/w β-pinene.
In one aspect, the essential oil further comprises from 20 to 30% w/w limonene.
In one aspect, the essential oil further comprises from 7 to 12% w/w beta-caryophyllene.
In one aspect, the essential oil further comprises less than 3% w/w piperine.

One aspect presented herein provides an essential oil extracted from ginger root, wherein the essential oil comprises at least 13% w/w eucalyptol.
In one aspect, the essential oil comprises from 13 to 15% w/w eucalyptol.
In one aspect, the essential oil comprises from 2 to 6% w/w 6-methyl-5-hepten-2-one.
In one aspect, the essential oil comprises from 19 to 25% w/w neral.
In one aspect, the essential oil comprises from 26 to 29% w/w geranial.
In one aspect, the essential oil comprises greater than 0.1% w/w 2-heptanone.
In one aspect, the essential oil comprises greater than 0.2% w/w nerol.
In one aspect, the essential oil comprises less than 1% w/w geraniol.
In one aspect, the essential oil comprises less than 18.5% w/w zingiberene.

One aspect presented herein provides an extract from pears, wherein the extract comprises at least 0.1% w/w hexyl acetate.
In one aspect, the extract comprises from 0.1 to 6% w/w hexyl acetate.
In one aspect, the extract further comprises from 3 to 15% w/w acetol.
In one aspect, the extract further comprises from 2 to 8% w/w acetic acid.
In one aspect, the extract further comprises from 0.5 to 2% w/w furfural.
In one aspect, the extract further comprises from 0.5 to 2% w/w furfural alcohol.
In one aspect, the extract further comprises from 0.2 to 2% w/w 2-methylbutyric acid.
In one aspect, the extract further comprises from 6 to 46% w/w 1,3-dihydroxyacetone.

In one aspect, the extract further comprises from 0.2 to 7% w/w 1,3-octanediol.

In one aspect, the extract further comprises from 0.5 to 4% w/w 5-hydroxy-5,6-dihydrolmaltol.

In one aspect, the extract further comprises from 1 to 4% w/w 5-hydroxymethyl furfural.

One aspect presented herein provides an extract from green tea leaves, wherein the extract comprises at least 12% w/w caffeine.

In one aspect, the extract comprises from 12 to 30% w/w caffeine.

In one aspect, the extract further comprises less than 8% furfuryl alcohol.

In one aspect, the extract further comprises 3,5-octadien-2-one, β-ionone, and 4,5-epoxy-β-ionone.

One aspect presented herein provides an extract from roasted coffee beans, wherein the extract comprises at least 2% w/w coffee furanone.

In one aspect, the extract comprises from 2 to 2.5% w/w coffee furanone.

In one aspect, the extract further comprises from 3 to 4% w/w 2-methyl pyrazine.

In one aspect, the extract further comprises from 0.5 to 2% w/w acetylmethyl carbinol.

In one aspect, the extract further comprises from 0.5 to 8% w/w acetol.

In one aspect, the extract further comprises from 35 to 45% w/w furfuryl alcohol.

In one aspect, the extract further comprises 0.2% w/w 2-cyclopentenone.

One aspect presented herein provides an extract, wherein the extract is obtained via a method according to any one of the aspects presented herein.

One aspect presented herein provides a perfumed article containing the extract according to some aspects presented herein, wherein the perfumed article is selected from the group consisting of: an aromatic water, a perfume, a cologne, a bath gel, a shower gel, a shampoo, a hair care product, a cosmetic preparation, a deodorant, an air freshener, a detergent, a fabric softener, and a household cleaner.

DETAILED DESCRIPTION

In the following description, reference is made to specific embodiments which may be practiced, which is shown by way of illustration. These embodiments are described in detail to enable those skilled in the art to practice the invention described herein, and it is to be understood that other embodiments may be utilized and that logical changes may be made without departing from the scope of the aspects presented herein. The following description of example embodiments is, therefore, not to be taken in a limited sense, and the scope of the various aspects presented herein is defined by the appended claims.

The Abstract is provided to comply with 37 C.F.R. § 1.72(b) to allow the reader to quickly ascertain the nature and gist of the technical disclosure. The Abstract is submitted with the understanding that it will not be used to interpret or limit the scope or meaning of the claims.

The Method According to Some Aspects Presented Herein

Without intending to be limited to any particular theory, conventional methods to obtain extracts, such as, for example, essential oils from plant biomass frequently require the use of solvents that may be harmful to the environment, and/or humans. Furthermore, conventional methods frequently require large volumes of solvent to achieve acceptable yields of the extract. While microwave assisted extraction may overcome some of the limitations of conventional extraction methods, microwave assisted methods of obtaining extracts, such as, essential oils from plant biomass has had limited commercial development. Problems encountered in scaling up microwave assisted extraction methods up to an industrial scale include, for example, consistently obtaining extracts from a large volume of plant biomass. Additionally, the olfactive properties of the extract are frequently altered by the extraction process. Alterations may be caused by several factors, including, but not limited to the presence, or enrichment of compounds having undesirable olfactive notes. Other alterations may be the absence, or reduction of compounds having the desired olfactive notes.

Consequently, there is a need for microwave assisted extraction methods at an industrial scale that are capable of generating an extract, such as an essential oil with improved olfactive properties.

Figure 1:
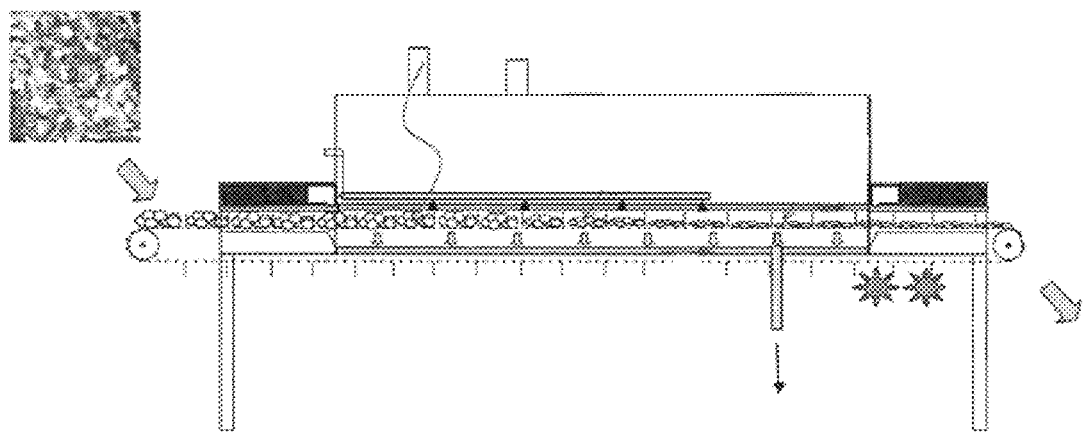
FIG. 1 shows a representation of apparatus for extracting essential oils from plant biomass according to some aspects presented herein.
Figure 2:
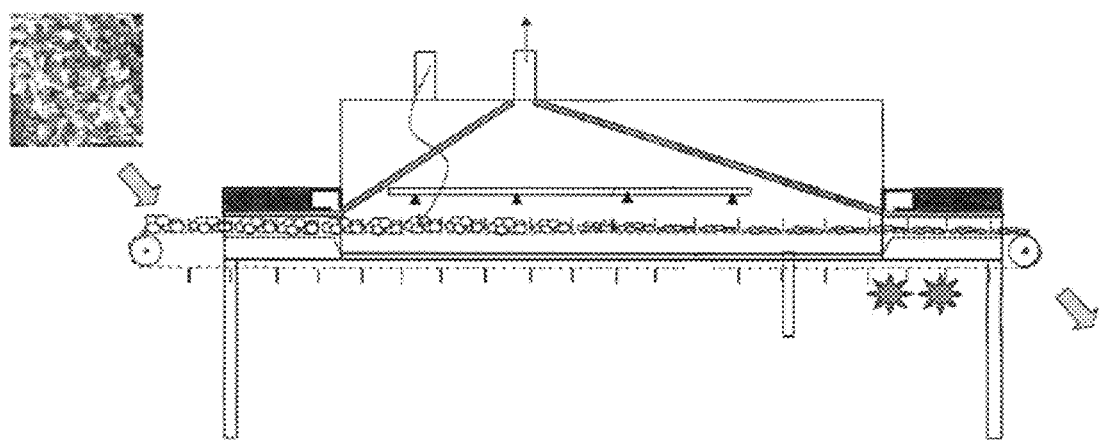
FIG. 2 shows a representation of apparatus for extracting essential oils from plant biomass according to some aspects presented herein.

Referring to FIGS. 1 and 2, the present disclosure provides a continuous extraction method, wherein plant biomass is continually introduced into a vessel at one end, and subjected to microwave energy to vaporize the water present in the biomass, thereby producing a distillate. In some aspects, the distillate contains the desired extract. In some aspects, the extract is an essential oil. In the aspects shown in FIGS. 1 and 2, the treated plant biomass is expelled from the vessel at the opposite end.

The apparatus shown in FIGS. 1 and 2 may be scaled up. For example, the length of the conveyor belt, the length of the vessel, and/or the velocity of the conveyor belt may be increased, or decreased, depending on the quantity of the plant biomass to be processed and/or the desired volume of the extract.

Without intending to be limited to any particular theory, the methods and apparatus presented herein do not require the addition of solvents, and produce extracts, essential oils having improved olfactive profiles. In some aspects, the improved olfactive profile may be an olfactive profile the same, or highly similar to the fresh plant. Alternatively, the improved olfactive profile may be an olfactive profile having fewer artefacts, such as, for example, undesired olfactive notes.

The apparatus shown in FIGS. 1 and 2 may be modified. Modifications include configurations to allow classical hydro-distillation. Another example of a modification may be a configuration to allow collection of the distillate via gravimetry.

Another example of a modification may be the application of exogenous steam. In some aspects, the flow of steam may also be modified.

Another example of a modification may be the recycling of the distillate within the vessel, such as, for example, via cohobation, to concentrate the distillate. An example of cohobation is disclosed in French Patent Application Publication No. FR3003181 A1.

Another example of a modification may be a depression in the inner vessel, wherein the depression allows the distillate to collect and be removed by gravimetry.

Figure 3:
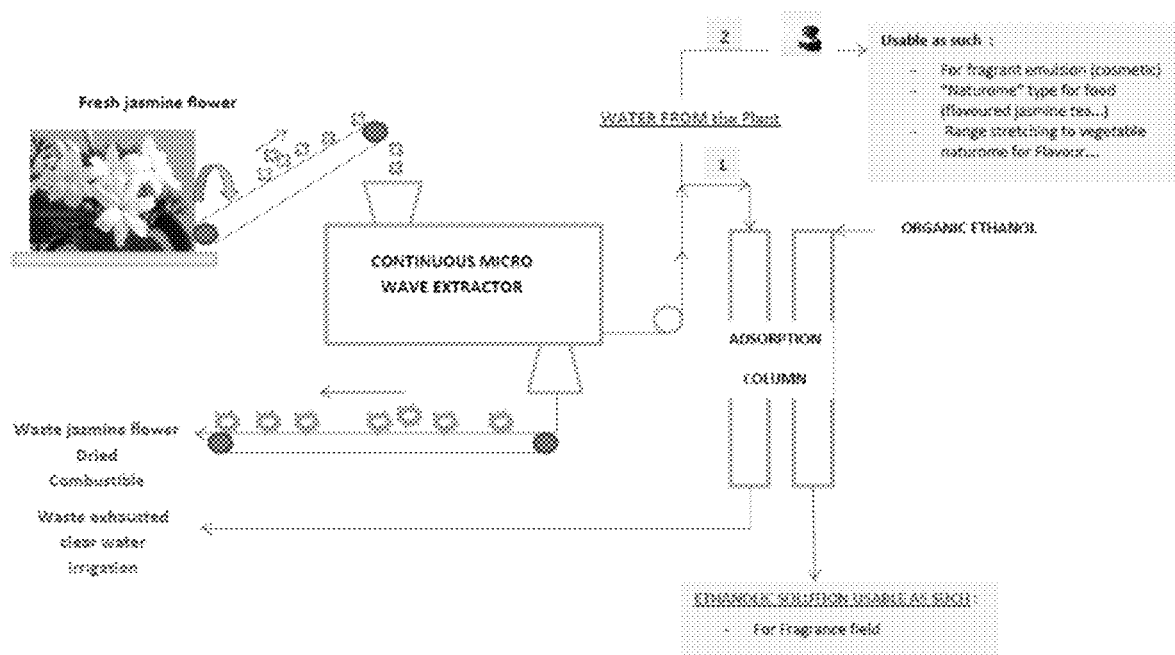
FIG. 3 shows a representation of a method according to some aspects presented herein.

Referring to FIG. 3, in some aspects, the present disclosure provides a process, wherein plant biomass is introduced into a vessel and subjected to microwave energy to vaporize the water present in the biomass, thereby producing a distillate. In the aspect shown in FIG. 3, the distillate is collected by gravimetry.

In some aspects, the distillate is used, without any additional processing. Alternatively, in some aspects, the distillate is further processed.

Examples of further processing include, but are not limited to, concentration, drying, thin-film distillation, resin-based chromatography, and the like.

In some aspects, the essential oils are purified from the distillate by decanting the oil from the aqueous phase of the distillate.

In some aspects, the distillate is adsorbed onto a column, and eluted off with a solvent, with a flow of 3 to10 bed volumes per hour.

In some aspects, the flow may be from 4 to 10, alternatively, from 5 to 10, alternatively, from 6 to 10, alternatively, from 7 to 10, alternatively, from 8 to 10, alternatively, from 9 to 10 bed volumes per hour.

In some aspects, the flow may be from 4 to 9, alternatively, from 4 to 8, alternatively, from 4 to 7, alternatively, from 4 to 6, alternatively, from 4 to 5 bed volumes per hour.

In some aspects, the flow may be 3, or 4, or 5, or 6, or 7, or 8, or 9, or 10 bed volumes per hour.

For example, in the aspect presented in FIG. 3, the distillate is adsorbed onto a XAD4 resin column, and eluted off with ethanol, with a flow of 5 bed volumes per hour.

Other solvents include but are not limited to, steam, supercritical $CO_2$, and the like.

Other resins include, but are not limited to XAD16, and the like.

In some aspects, the apparatus and methods disclosed herein provide a method for the continuous extraction, not batch-based extraction of extracts, such as, for example, essential oils from plant biomass. Without intending to be limited to any particular theory, the apparatus and methods disclosed result in smaller lot to lot variation of the extract. Moreover, the parameters of the apparatus and methods disclosed herein may be adjusted to alter the properties of the distillate, and thus the extract obtained. Adjustments include, but are not limited to, the first velocity of the conveyer belt, the length of the conveyer belt, the first intensity of the microwave energy, the length of the vessel, the temperature within the vessel, the rate of addition of the plant biomass, the time sufficient to treat the plant biomass, or any combination thereof.

Without intending to be limited to any particular theory, the methods and apparatus presented herein may produce a smaller amount of non-recyclable waste, compared to other methods in the art. In addition, the methods and apparatus presented herein may have a smaller $CO_2$ footprint, compared to other methods in the art.

Additionally, the methods and apparatus presented herein may be more energy efficient, compared to other methods in the art.

Additionally, the methods and apparatus presented herein may produce essential oils faster, compared to other methods in the art.

Accordingly, some presented herein provides a method, wherein the method obtains an extract from plant biomass,
wherein the method comprises the steps of:
 a. obtaining the plant biomass;
 b. subjecting the plant biomass to microwave energy, of a first intensity, for a time sufficient to heat the biomass to a temperature to vaporize water within the biomass, thereby producing a distillate; and
 c. collecting the distillate.

Some aspects presented herein provide a method, wherein the method obtains an extract from plant biomass,
wherein the method comprises the steps of:
 a. obtaining the plant biomass;
 b. placing the plant biomass onto a conveyor belt, having a length, and introducing the plant biomass into a vessel having length, via the conveyor belt,
  wherein the plant biomass is introduced into the vessel by moving the conveyer belt at a first velocity, and
  wherein the plant biomass is introduced into the vessel at a rate;
 c. subjecting the plant biomass to microwave energy, of a first intensity, for a time sufficient to heat the biomass to a temperature to vaporize water within the biomass, thereby producing a distillate; and
 d. collecting the distillate.

In some aspects, the extract comprises an essential oil.

In some aspects, the time sufficient to heat the biomass to a temperature to vaporize water is controlled by the first velocity of the conveyer belt, the length of the conveyer belt, the first intensity of the microwave energy, the length of the vessel, or any combination thereof.

Accordingly, in some aspects, the length of the conveyor belt is at least 1 meter. In some aspects, the length of the conveyor belt is at least 1.5, or at least 2, or at least 2.5, or at least 3, or at least 3.5, or at least 4, or at least 4.5, or at least 5, or at least 5.5, or at least 6, or at least 6.5, or at least 7, or at least 7.5, or at least 8, or at least 8.5, or at least 9, or at least 9.5, or at least 10 meters.

Similarly, in some aspects, the length of the vessel is at least 1 meter. In some aspects, the length of the vessel is at least 1.5, or at least 2, or at least 2.5, or at least 3, or at least 3.5, or at least 4, or at least 4.5, or at least 5, or at least 5.5, or at least 6, or at least 6.5, or at least 7, or at least 7.5, or at least 8, or at least 8.5, or at least 9, or at least 9.5, or at least 10 meters.

In some aspects, the plant biomass is introduced at a rate greater than or equal to 12 Kg/hour. In some aspects, the plant biomass is introduced at a rate from 0.5 to 12 Kg/hour. In some aspects, the plant biomass is introduced at a rate from 0.5 to 11.5 Kg/hour. In some aspects, the plant biomass is introduced at a rate from 0.5 to 11 Kg/hour. In some aspects, the plant biomass is introduced at a rate from 0.5 to 10.5 Kg/hour. In some aspects, the plant biomass is introduced at a rate from 0.5 to 10 Kg/hour. In some aspects, the plant biomass is introduced at a rate from 0.5 to 9.5 Kg/hour. In some aspects, the plant biomass is introduced at a rate from 0.5 to 9 Kg/hour. In some aspects, the plant biomass is introduced at a rate from 0.5 to 8.5 Kg/hour. In some aspects, the plant biomass is introduced at a rate from 0.5 to 8 Kg/hour. In some aspects, the plant biomass is introduced at a rate from 0.5 to 7.5 Kg/hour. In some aspects, the plant biomass is introduced at a rate from 0.5 to 7 Kg/hour. In some aspects, the plant biomass is introduced at a rate from 0.5 to 6.5 Kg/hour. In some aspects, the plant biomass is introduced at a rate from 0.5 to 6 Kg/hour. In some aspects, the plant biomass is introduced at a rate from 0.5 to 5.5 Kg/hour. In some aspects, the plant biomass is introduced at a rate from 0.5 to 5 Kg/hour. In some aspects, the plant biomass is introduced at a rate from 0.5 to 4.5 Kg/hour. In some aspects, the plant biomass is introduced at a rate from 0.5 to 4 Kg/hour. In some aspects, the plant biomass is introduced at a rate from 0.5 to 3.5 Kg/hour. In some aspects, the plant biomass is introduced at a rate from 0.5 to 3 Kg/hour. In some aspects, the plant biomass is introduced at a rate from 0.5 to 2.5 Kg/hour. In some aspects, the plant biomass is introduced at a rate from 0.5 to 2 Kg/hour. In some aspects, the plant biomass is introduced at a rate from 0.5 to 1.5 Kg/hour. In some aspects, the plant biomass is introduced at a rate from 0.5 to 1 Kg/hour.

In some aspects, the plant biomass is introduced at a rate from 1 to 12 Kg/hour. In some aspects, the plant biomass is introduced at a rate from 1.5 to 12 Kg/hour. In some aspects, the plant biomass is introduced at a rate from 2 to 12 Kg/hour. In some aspects, the plant biomass is introduced at a rate from 2.5 to 12 Kg/hour. In some aspects, the plant biomass is introduced at a rate from 3 to 12 Kg/hour. In some aspects, the plant biomass is introduced at a rate from 3.5 to 12 Kg/hour. In some aspects, the plant biomass is introduced at a rate from 4 to 12 Kg/hour. In some aspects, the plant biomass is introduced at a rate from 4.5 to 12 Kg/hour. In some aspects, the plant biomass is introduced at a rate from 5 to 12 Kg/hour. In some aspects, the plant biomass is introduced at a rate from 5.5 to 12 Kg/hour. In some aspects, the plant biomass is introduced at a rate from 6 to 12 Kg/hour. In some aspects, the plant biomass is introduced at a rate from 6.5 to 12 Kg/hour. In some aspects, the plant biomass is introduced at a rate from 7 to 12 Kg/hour. In some aspects, the plant biomass is introduced at a rate from 7.5 to 12 Kg/hour. In some aspects, the plant biomass is introduced at a rate from 8 to 12 Kg/hour. In some aspects, the plant biomass is introduced at a rate from 8.5 to 12 Kg/hour. In some aspects, the plant biomass is introduced at a rate from 9 to 12 Kg/hour. In some aspects, the plant biomass is introduced at a rate from 9.5 to 12 Kg/hour. In some aspects, the plant biomass is introduced at a rate from 10 to 12 Kg/hour. In some aspects, the plant biomass is introduced at a rate from 10.5 to 12 Kg/hour. In some aspects, the plant biomass is introduced at a rate from 11 to 12 Kg/hour. In some aspects, the plant biomass is introduced at a rate from 11.5 to 12 Kg/hour.

In some aspects, the plant biomass is introduced at 0.5, or 1, or 1.5, or 2, or 2.5, or 3, or 3.5, or 4, or 4.5, or 5, or 5.5, or 6, or 6.5, or 7, or 7.5, or 8, or 8.5, or 9, or 9.5, or 10, or 10.5, or 11, or 11.5, or 12 Kg per hour.

In some aspects, the plant biomass is introduced into the vessel at a rate of at least 4 Kg of plant biomass per hour.

In some aspects, the time sufficient is from 20 to 45 minutes. In some aspects, the time sufficient is from 25 to 45 minutes. In some aspects, the time sufficient is from 30 to 45 minutes. In some aspects, the time sufficient is from 35 to 45 minutes. In some aspects, the time sufficient is from 40 to 45 minutes.

In some aspects, the time sufficient is from 20 to 40 minutes. In some aspects, the time sufficient is from 25 to 35 minutes. In some aspects, the time sufficient is from 20 to 30 minutes. In some aspects, the time sufficient is from 20 to 25 minutes.

In some aspects, the time sufficient is 20, or 25, or 30, or 35, or 40, or 45 minutes.

In some aspects, the first intensity of the microwave energy is from 100 to 3000 Watts. In some aspects, the first intensity of the microwave energy is from 100 to 2900 Watts. In some aspects, the first intensity of the microwave energy is from 100 to 2800 Watts. In some aspects, the first intensity of the microwave energy is from 100 to 2700 Watts. In some aspects, the first intensity of the microwave energy is from 100 to 2600 Watts. In some aspects, the first intensity of the microwave energy is from 100 to 2500 Watts. In some aspects, the first intensity of the microwave energy is from 100 to 2400 Watts. In some aspects, the first intensity of the microwave energy is from 100 to 2300 Watts. In some aspects, the first intensity of the microwave energy is from 100 to 2200 Watts. In some aspects, the first intensity of the microwave energy is from 100 to 2100 Watts. In some aspects, the first intensity of the microwave energy is from 100 to 2000 Watts. In some aspects, the first intensity of the microwave energy is from 100 to 1900 Watts. In some aspects, the first intensity of the microwave energy is from 100 to 1800 Watts. In some aspects, the first intensity of the microwave energy is from 100 to 1700 Watts. In some aspects, the first intensity of the microwave energy is from 100 to 1600 Watts. In some aspects, the first intensity of the microwave energy is from 100 to 1500 Watts. In some aspects, the first intensity of the microwave energy is from 100 to 1400 Watts. In some aspects, the first intensity of the microwave energy is from 100 to 1300 Watts. In some aspects, the first intensity of the microwave energy is from 100 to 1200 Watts. In some aspects, the first intensity of the microwave energy is from 100 to 1100 Watts. In some aspects, the first intensity of the microwave energy is from 100 to 1000 Watts. In some aspects, the first intensity of the microwave energy is from 100 to 900 Watts. In some aspects, the first intensity of the microwave energy is from 100 to 800 Watts. In some aspects, the first intensity of the microwave energy is from 100 to 700 Watts. In some aspects, the first intensity of the microwave energy is from 100 to 600 Watts. In some aspects, the first intensity of the microwave energy is from 100 to 500 Watts. In some aspects, the first intensity of the microwave energy is from 100 to 400 Watts. In some aspects, the first intensity of the microwave energy is from 100 to 300 Watts. In some aspects, the first intensity of the microwave energy is from 100 to 200 Watts.

In some aspects, the first intensity of the microwave energy is from 200 to 3000 Watts. In some aspects, the first intensity of the microwave energy is from 300 to 3000 Watts. In some aspects, the first intensity of the microwave energy is from 400 to 3000 Watts. In some aspects, the first intensity of the microwave energy is from 500 to 3000 Watts. In some aspects, the first intensity of the microwave energy is from 600 to 3000 Watts. In some aspects, the first intensity of the microwave energy is from 700 to 3000 Watts. In some aspects, the first intensity of the microwave energy is from 800 to 3000 Watts. In some aspects, the first intensity of the microwave energy is from 900 to 3000 Watts. In some aspects, the first intensity of the microwave energy is from 1000 to 3000 Watts. In some aspects, the first intensity of the microwave energy is from 1100 to 3000 Watts. In some aspects, the first intensity of the microwave energy is from 1200 to 3000 Watts. In some aspects, the first intensity of the microwave energy is from 1300 to 3000 Watts. In some aspects, the first intensity of the microwave energy is from 1400 to 3000 Watts. In some aspects, the first intensity of the microwave energy is from 1500 to 3000 Watts. In some aspects, the first intensity of the microwave energy is from 1600 to 3000 Watts. In some aspects, the first intensity of the microwave energy is from 1700 to 3000 Watts. In some aspects, the first intensity of the microwave energy is from 1800 to 3000 Watts. In some aspects, the first intensity of the microwave energy is from 1900 to 3000 Watts. In some aspects, the first intensity of the microwave energy is from 2000 to 3000 Watts. In some aspects, the first intensity of the microwave energy is from 2100 to 3000 Watts. In some aspects, the first intensity of the microwave energy is from 2200 to 3000 Watts. In some aspects, the first intensity of the microwave energy is from 2300 to 3000 Watts. In some aspects, the first intensity of the microwave energy is from 2400 to 3000 Watts. In some aspects, the first intensity of the microwave energy is from 2500 to 3000 Watts. In some aspects, the first intensity of the microwave energy is from 2600 to 3000 Watts. In some aspects, the first intensity of the microwave energy is from 2700 to 3000 Watts. In some aspects, the first intensity of the microwave energy is from 2800 to 3000 Watts. In some aspects, the first intensity of the microwave energy is from 2900 to 3000 Watts.

In some aspects, the first intensity of the microwave energy is 200, or 300, or 400, or 500, or 600, or 700, or 800, or 900, or 1000, or 1100, or 1200, or 1300, or 1400, or 1500, or 1600, or 1700, or 1800, or 1900, or 2000, or 2100, or 2200, or 2300, or 2400, or 2500, or 2600, or 2700, or 2800, or 2900, or 3000 Watts.

In some aspects, the first intensity of the microwave energy is 200 Watts. In some aspects, the first intensity is less than 200 Watts. In some aspects, the first intensity is an intensity sufficient to vaporize water within the biomass.

In some aspects, the first intensity of the microwave energy is from 0.2 KWH/Kg biomass to 0.6 KWH/Kg biomass. In some aspects, the first intensity of the microwave energy is from 0.25 KWH/Kg biomass to 0.6 KWH/Kg biomass. In some aspects, the first intensity of the microwave energy is from 0.3 KWH/Kg biomass to 0.6 KWH/Kg biomass. In some aspects, the first intensity of the microwave energy is from 0.35 KWH/Kg biomass to 0.6 KWH/Kg biomass. In some aspects, the first intensity of the microwave energy is from 0.4 KWH/Kg biomass to 0.6 KWH/Kg biomass. In some aspects, the first intensity of the microwave energy is from 0.45 KWH/Kg biomass to 0.6 KWH/Kg biomass. In some aspects, the first intensity of the microwave energy is from 0.3 KWH/Kg biomass to 0.5 KWH/Kg biomass. In some aspects, the first intensity of the microwave energy is from 0.55 KWH/Kg biomass to 0.6 KWH/Kg biomass.

In some aspects, the first intensity of the microwave energy is from 0.2 KWH/Kg biomass to 0.55 KWH/Kg biomass. In some aspects, the first intensity of the microwave energy is from 0.2 KWH/Kg biomass to 0.5 KWH/Kg biomass. In some aspects, the first intensity of the microwave energy is from 0.2 KWH/Kg biomass to 0.45 KWH/Kg biomass. In some aspects, the first intensity of the microwave energy is from 0.2 KWH/Kg biomass to 0.4 KWH/Kg biomass. In some aspects, the first intensity of the microwave energy is from 0.2 KWH/Kg biomass to 0.35 KWH/Kg biomass. In some aspects, the first intensity of the microwave energy is from 0.2 KWH/Kg biomass to 0.3 KWH/Kg biomass. In some aspects, the first intensity of the microwave energy is from 0.2 KWH/Kg biomass to 0.25 KWH/Kg biomass.

In some aspects, the first intensity of the microwave energy is 0.2, or 0.25, or 0.3, or 0.35, or 0.4, or 0.45, or 0.5, or 0.55, or 0.6 KWH/Kg biomass.

In some aspects, the first intensity may be either increased, or alternatively, decreased to a second intensity during the method.

In some aspects, the temperature of the inside of the vessel is from 40 to 100 degrees Celsius. In some aspects, the temperature of the inside of the vessel is from 40 to 90 degrees Celsius. In some aspects, the temperature of the inside of the vessel is from 40 to 80 degrees Celsius. In some aspects, the temperature of the inside of the vessel is from 40 to 70 degrees Celsius. In some aspects, the temperature of the inside of the vessel is from 40 to 60 degrees Celsius. In some aspects, the temperature of the inside of the vessel is from 40 to 50 degrees Celsius.

In some aspects, the temperature of the inside of the vessel is from 50 to 100 degrees Celsius. In some aspects, the temperature of the inside of the vessel is from 60 to 100 degrees Celsius. In some aspects, the temperature of the inside of the vessel is from 70 to 100 degrees Celsius. In some aspects, the temperature of the inside of the vessel is from 80 to 100 degrees Celsius. In some aspects, the temperature of the inside of the vessel is from 90 to 100 degrees Celsius.

In some aspects, the temperature of the inside of the vessel is from 60 to 80 degrees Celsius.

In some aspects, the temperature of the inside of the vessel is 40, or 50, or 60, or 70, or 80, or 90, or 100 degrees Celsius.

In some aspects the temperature of the inside of the vessel may be either increased, or alternatively, decreased to a second temperature during the method.

In some aspects, the collected distillate comprises an aqueous extract. In some aspects, the collected distillate comprises an essential oil. In some aspects, the essential oil is obtained from the aqueous extract.

In some aspects, the collected distillate comprises from 200 to 3000 ppm essential oils. In some aspects, the collected distillate comprises from 200 to 2900 ppm essential oils. In some aspects, the collected distillate comprises from 200 to 2800 ppm essential oils. In some aspects, the collected distillate comprises from 200 to 2700 ppm essential oils. In some aspects, the collected distillate comprises from 200 to 2600 ppm essential oils. In some aspects, the collected distillate comprises from 200 to 2500 ppm essential oils. In some aspects, the collected distillate comprises from 200 to 2400 ppm essential oils. In some aspects, the collected distillate comprises from 200 to 2300 ppm essential oils. In some aspects, the collected distillate comprises from 200 to 2200 ppm essential oils. In some aspects, the collected distillate comprises from 200 to 2100 ppm essential oils. In some aspects, the collected distillate comprises from 200 to 2000 ppm essential oils. In some aspects, the collected distillate comprises from 200 to 1900 ppm essential oils. In some aspects, the collected distillate comprises from 200 to 1800 ppm essential oils. In some aspects, the collected distillate comprises from 200 to 1700 ppm essential oils. In some aspects, the collected distillate comprises from 200 to 1600 ppm essential oils. In some aspects, the collected distillate comprises from 200 to 1500 ppm essential oils. In some aspects, the collected distillate comprises from 200 to 1400 ppm essential oils. In some aspects, the collected distillate comprises from 200 to 1300 ppm essential oils. In some aspects, the collected distillate comprises from 200 to 1200 ppm essential oils. In some aspects, the collected distillate comprises from 200 to 1100 ppm essential oils. In some aspects, the collected distillate comprises from 200 to 1000 ppm essential oils. In some aspects, the collected distillate comprises from 200 to 900 ppm essential oils. In some aspects, the collected distillate comprises from 200 to 800 ppm essential oils. In some aspects, the collected distillate comprises from 200 to 700 ppm essential oils. In some aspects, the collected distillate comprises from 200 to 600 ppm essential oils. In some aspects, the collected distillate comprises from 200 to 500 ppm essential oils. In some aspects, the collected distillate comprises from 200 to 400 ppm essential oils. In some aspects, the collected distillate comprises from 200 to 300 ppm essential oils.

In some aspects, the collected distillate comprises from 300 to 3000 ppm essential oils. In some aspects, the collected distillate comprises from 400 to 3000 ppm essential oils. In some aspects, the collected distillate comprises from 500 to 3000 ppm essential oils. In some aspects, the collected distillate comprises from 600 to 3000 ppm essential oils. In some aspects, the collected distillate comprises from 700 to 3000 ppm essential oils. In some aspects, the collected distillate comprises from 800 to 3000 ppm essential oils. In some aspects, the collected distillate comprises from 900 to 3000 ppm essential oils. In some aspects, the collected distillate comprises from 1000 to 3000 ppm essential oils. In some aspects, the collected distillate comprises from 1100 to 3000 ppm essential oils. In some aspects, the collected distillate comprises from 1200 to 3000 ppm essential oils. In some aspects, the collected distillate comprises from 1300 to 3000 ppm essential oils. In some aspects, the collected distillate comprises from 1400 to 3000 ppm essential oils. In some aspects, the collected distillate comprises from 1500 to 3000 ppm essential oils. In some aspects, the collected distillate comprises from 1600 to 3000 ppm essential oils. In some aspects, the collected distillate comprises from 1700 to 3000 ppm essential oils. In some aspects, the collected distillate comprises from 1800 to 3000 ppm essential oils. In some aspects, the collected distillate comprises from 1900 to 3000 ppm essential oils. In some aspects, the collected distillate comprises from 2000 to 3000 ppm essential oils. In some aspects, the collected distillate comprises from 2100 to 3000 ppm essential oils. In some aspects, the collected distillate comprises from 2200 to 3000 ppm essential oils. In some aspects, the collected distillate comprises from 2300 to 3000 ppm essential oils. In some aspects, the collected distillate comprises from 2400 to 3000 ppm essential oils. In some aspects, the collected distillate comprises from 2500 to 3000 ppm essential oils. In some aspects, the collected distillate comprises from 2600 to 3000 ppm essential oils. In some aspects, the collected distillate comprises from 2700 to 3000 ppm essential oils. In some aspects, the collected distillate comprises from 2800 to 3000 ppm essential oils. In some aspects, the collected distillate comprises from 2900 to 3000 ppm essential oils.

In some aspects, the collected distillate comprises 200, or 300, or 400, or 500, or 600, or 700, or 800, or 900, or 1000, or 1100, or 1200, or 1300, or 1400, or 1500, or 1600, or 1700, or 1800, or 1900, or 2000, or 2100, or 2200, or 2300, or 2400, or 2500, or 2600, or 2700, or 2800, or 2900, or 3000 ppm essential oils.

In some aspects, the collected distillate is further processed, thereby resulting in a composition comprising from 200 to 3000 ppm essential oils. In some aspects, the composition comprises from 200 to 2900 ppm essential oils. In some aspects, the composition comprises from 200 to 2800 ppm essential oils. In some aspects, the composition comprises from 200 to 2700 ppm essential oils. In some aspects, the composition comprises from 200 to 2600 ppm essential oils. In some aspects, the composition comprises from 200 to 2500 ppm essential oils. In some aspects, the composition comprises from 200 to 2400 ppm essential oils. In some aspects, the composition comprises from 200 to 2300 ppm essential oils. In some aspects, the composition comprises from 200 to 2200 ppm essential oils. In some aspects, the composition comprises from 200 to 2100 ppm essential oils. In some aspects, the composition comprises from 200 to 2000 ppm essential oils. In some aspects, the composition comprises from 200 to 1900 ppm essential oils. In some aspects, the composition comprises from 200 to 1800 ppm essential oils. In some aspects, the composition comprises from 200 to 1700 ppm essential oils. In some aspects, the composition comprises from 200 to 1600 ppm essential oils. In some aspects, the composition comprises from 200 to 1500 ppm essential oils. In some aspects, the composition comprises from 200 to 1400 ppm essential oils. In some aspects, the composition comprises from 200 to 1300 ppm essential oils. In some aspects, the composition comprises from 200 to 1200 ppm essential oils. In some aspects, the composition comprises from 200 to 1100 ppm essential oils. In some aspects, the composition comprises from 200 to 1000 ppm essential oils. In some aspects, the composition comprises from 200 to 900 ppm essential oils. In some aspects, the composition comprises from 200 to 800 ppm essential oils. In some aspects, the composition comprises from 200 to 700 ppm essential oils. In some aspects, the composition comprises from 200 to 600 ppm essential oils. In some aspects, the composition comprises from 200 to 500 ppm essential oils. In some aspects, the composition comprises from 200 to 400 ppm essential oils. In some aspects, the composition comprises from 200 to 300 ppm essential oils.

In some aspects, the composition comprises from 300 to 3000 ppm essential oils. In some aspects, the composition comprises from 400 to 3000 ppm essential oils. In some aspects, the composition comprises from 500 to 3000 ppm essential oils. In some aspects, the composition comprises from 600 to 3000 ppm essential oils. In some aspects, the composition comprises from 700 to 3000 ppm essential oils. In some aspects, the composition comprises from 800 to 3000 ppm essential oils. In some aspects, the composition comprises from 900 to 3000 ppm essential oils. In some aspects, the composition comprises from 1000 to 3000 ppm essential oils. In some aspects, the composition comprises from 1100 to 3000 ppm essential oils. In some aspects, the composition comprises from 1200 to 3000 ppm essential oils. In some aspects, the composition comprises from 1300 to 3000 ppm essential oils. In some aspects, the composition comprises from 1400 to 3000 ppm essential oils. In some aspects, the composition comprises from 1500 to 3000 ppm essential oils. In some aspects, the composition comprises from 1600 to 3000 ppm essential oils. In some aspects, the composition comprises from 1700 to 3000 ppm essential oils. In some aspects, the composition comprises from 1800 to 3000 ppm essential oils. In some aspects, the composition comprises from 1900 to 3000 ppm essential oils. In some aspects, the composition comprises from 2000 to 3000 ppm essential oils. In some aspects, the composition comprises from 2100 to 3000 ppm essential oils. In some aspects, the composition comprises from 2200 to 3000 ppm essential oils. In some aspects, the composition comprises from 2300 to 3000 ppm essential oils. In some aspects, the composition comprises from 2400 to 3000 ppm essential oils. In some aspects, the composition comprises from 2500 to 3000 ppm essential oils. In some aspects, the composition comprises from 2600 to 3000 ppm essential oils. In some aspects, the composition comprises from 2700 to 3000 ppm essential oils. In some aspects, the composition comprises from 2800 to 3000 ppm essential oils. In some aspects, the composition comprises from 2900 to 3000 ppm essential oils.

In some aspects, the composition comprises 200, or 300, or 400, or 500, or 600, or 700, or 800, or 900, or 1000, or 1100, or 1200, or 1300, or 1400, or 1500, or 1600, or 1700, or 1800, or 1900, or 2000, or 2100, or 2200, or 2300, or 2400, or 2500, or 2600, or 2700, or 2800, or 2900, or 3000 ppm essential oils.

The Plant Biomass According to Some Aspects Presented Herein

As used herein, the term "biomass" refers to organic material isolated, derived, or obtained from plants. Plant biomass may be isolated, derived, or obtained from any part of the plant, such as, for example, the leaves, the flowers, the stems, the roots, the fruit, the entire plant, the seeds, or any combination thereof.

The plant biomass may be freshly obtained, or, alternatively, the plant biomass may be dried. As used herein, the term "freshly obtained" refers to plant biomass that retains all, or greater than 90% of its intrinsic water.

In some aspects, the plant biomass retains from 50 to 90% of its intrinsic water. In some aspects, the plant biomass retains from 55 to 90% of its intrinsic water. In some aspects, the plant biomass retains from 60 to 90% of its intrinsic water. In some aspects, the plant biomass retains from 65 to 90% of its intrinsic water. In some aspects, the plant biomass retains from 70 to 90% of its intrinsic water. In some aspects, the plant biomass retains from 75 to 90% of its intrinsic water. In some aspects, the plant biomass retains from 80 to 90% of its intrinsic water. In some aspects, the plant biomass retains from 85 to 90% of its intrinsic water.

In some aspects, the plant biomass retains from 50 to 85% of its intrinsic water. In some aspects, the plant biomass retains from 50 to 80% of its intrinsic water. In some aspects, the plant biomass retains from 50 to 75% of its intrinsic water. In some aspects, the plant biomass retains from 50 to 70% of its intrinsic water. In some aspects, the plant biomass retains from 50 to 65% of its intrinsic water. In some aspects, the plant biomass retains from 50 to 60% of its intrinsic water. In some aspects, the plant biomass retains from 50 to 55% of its intrinsic water.

In some aspects, the plant biomass retains 50, or 55, or 60, or 65, or 70, or 75, or 80, or 85, or 90, or 95% of its intrinsic water, or greater.

In some aspects, the plant biomass may be processed prior to treatment according to the methods presented herein. Examples of processing include, but are not limited to, cutting, chopping, grinding, crushing, wetting, and the like.

In some aspects, the water is added to the plant biomass to raise the moisture content to 90% or greater. In some aspects, the moisture content of the plant biomass after water has been added is from 50 to 90%. In some aspects, the moisture content of the plant biomass after water has been added is from 55 to 90%. In some aspects, the moisture content of the plant biomass after water has been added is from 60 to 90%. In some aspects, the moisture content of the plant biomass after water has been added is from 65 to 90%. In some aspects, the moisture content of the plant biomass after water has been added is from 70 to 90%. In some aspects, the moisture content of the plant biomass after water has been added is from 75 to 90%. In some aspects, the moisture content of the plant biomass after water has been added is from 80 to 90%. In some aspects, the moisture content of the plant biomass after water has been added is from 85 to 90%.

In some aspects, the moisture content of the plant biomass after water has been added is from 50 to 90%. In some aspects, the moisture content of the plant biomass after water has been added is from 50 to 85%. In some aspects, the moisture content of the plant biomass after water has been added is from 50 to 80%. In some aspects, the moisture content of the plant biomass after water has been added is from 50 to 75%. In some aspects, the moisture content of the plant biomass after water has been added is from 50 to 70%. In some aspects, the moisture content of the plant biomass after water has been added is from 50 to 65%. In some aspects, the moisture content of the plant biomass after water has been added is from 50 to 60%. In some aspects, the moisture content of the plant biomass after water has been added is from 50 to 55%.

In some aspects, the moisture content of the plant biomass after water has been added is 50, or 55, or 60, or 65, or 70, or 75, or 80, or 85, or 90, or 95%.

In some aspects, the plant biomass comprises freshly obtained flowers. In some aspects, the flowers are selected from the group consisting of: flowers from a plant of the genus *Oleaceae*, flowers from *Polianthes tuberosa*, flowers from a plant of the genus *Rosa*, flowers from Lilac plants, Flowers from Lily of the Valley plants, Flowers from Mock Orange plants, flowers from Honeysuckle plants, flowers from *Cananga odorata*, flowers from *Artabotrys odoratissimus*, and flowers from Wisteria plants.

In some aspects, the plant of the genus *Oleaceae* is a plant of the *Jasminium* species is selected from the group consisting of *Jasminium grandiflorum* and *Jasminium sambac*.

In some aspects, the plant biomass comprises freshly obtained fruit. In some aspects, the fruit comprises fruit from the genus *Pyrus*. In some aspects, the plant biomass comprises dried fruit, such as dried fruit from *Piper nigrum*. In some aspects, the plant biomass comprises roots, such as, for example the roots of *Zingiber officinale*. In some aspects, the plant biomass comprises leaves, such as, for example leaves from *Camellia sinensis*.

The Extracts According to Some Aspects Presented Herein

Referring to Examples 1 and 2 below, by way of illustration only, the methods and apparatus presented herein do not require the addition of solvents, and produce essential oils having improved olfactive profiles. In some aspects, the improved olfactive profile may be an olfactive profile the same, or highly similar to the fresh plant. Alternatively, the improved olfactive profile may be an olfactive profile having fewer artefacts, such as, for example, undesired olfactive notes.

While Examples 1 and 2 depict the use of the methods and apparatus presented herein using freshly isolated flowers from *Jasminium grandiflorum*, one of ordinary skill in the art may readily appreciate the application of the same methods and/or apparatus to other sources of plant biomass.

In some aspects, the improved olfactive profile may be an olfactive profile the same, or highly similar to the fresh plant. In some aspects, the improved olfactive profile may be a result of changes in the relative proportions of one, or more than one compound within the essential oil. By way of illustration, the essential oil described in Example 2 comprises at least 5% w/w (±)-3,7-Dimethyl-1,6-octadien-3-ol, at least 7% w/w (z)-jasmone, and at least 20% w/w benzyl acetate, wherein the levels of these compounds are higher compared to essential oils derived from *Jasminium grandiflorum*, using conventional methods.

In some aspects, the improved olfactive profile may be an olfactive profile having fewer artefacts, such as, for example, undesired olfactive notes. By way of illustration, the essential oil described in Example 2 comprises no more than 6% w/w benzyl benzoate, wherein the level of the compound is lower compared to essential oils derived from *Jasminium grandiflorum*, using conventional methods.

The olfactive profile of the essential oil may be determined by any method readily selected by one of ordinary skill in the art, such as, for example, sensory testing, chemical analysis, and the like.

Essential Oil Derived from *Jasminium grandiflorum:* One aspect presented herein provides an essential oil extracted from at least one plant of the *Jasminium* species, wherein the essential oil comprises at least 7% w/w (z)-jasmone.

In some aspects, the at least one plant of the *Jasminium* species is selected from the group consisting of *Jasminium grandiflorum* and *Jasminium sambac*.

Without intending to be limited to any particular theory, (z)-jasmone is a molecule that contributes to the jasmine flower scent, wherein essential oils having higher levels of (z)-jasmone would smell more like fresh jasmine flowers, compared to essential oils having lower levels of (z)-jasmone.

In some aspects, the essential oil comprises from 7 to 15% w/w (z)-jasmone, which is higher compared to essential oils derived from *Jasminium grandiflorum*, using conventional methods. Accordingly, the essential oil smells more like fresh jasmine flowers, compared to essential oils having lower levels of (z)-jasmone.

In some aspects, the essential oil comprises from 7 to 15% w/w (z)-jasmone. In some aspects, the essential oil comprises from 7 to 14% w/w (z)-jasmone. In some aspects, the essential oil comprises from 7 to 13% w/w (z)-jasmone. In some aspects, the essential oil comprises from 7 to 12% w/w (z)-jasmone. In some aspects, the essential oil comprises from 7 to 11% w/w (z)-jasmone. In some aspects, the essential oil comprises from 7 to 10% w/w (z)-jasmone. In some aspects, the essential oil comprises from 7 to 9% w/w (z)-jasmone. In some aspects, the essential oil comprises from 7 to 8% w/w (z)-jasmone.

In some aspects, the essential oil comprises from 8 to 15% w/w (z)-jasmone. In some aspects, the essential oil comprises from 9 to 15% w/w (z)-jasmone. In some aspects, the essential oil comprises from 10 to 15% w/w (z)-jasmone. In some aspects, the essential oil comprises from 11 to 15% w/w (z)-jasmone. In some aspects, the essential oil comprises from 12 to 15% w/w (z)-jasmone. In some aspects, the essential oil comprises from 13 to 15% w/w (z)-jasmone. In some aspects, the essential oil comprises from 14 to 15% w/w (z)-jasmone.

In some aspects, the essential oil comprises 7, or 8, or 9, or 10, or 11, or 12, or 13, or 14, or 15% w/w (z)-jasmone.

Other molecules that may contribute to the jasmine flower scent include (±)-3,7-Dimethyl-1,6-octadien-3-ol and benzyl acetate. In some aspects, the levels of either (±)-3,7-Dimethyl-1,6-octadien-3-ol and benzyl acetate, or both are higher compared to essential oils derived from *Jasminium grandiflorum*, using conventional methods. Accordingly, the essential oil smells more like fresh jasmine flowers, compared to essential oils having lower levels of (±)-3,7-Dimethyl-1,6-octadien-3-ol and benzyl acetate, w benzyl acetate, or both.

In some aspects, the essential oil further comprises from 10 to 20% w/w (±)-3,7-Dimethyl-1,6-octadien-3-ol. In some aspects, the essential oil further comprises from 10 to 19% w/w (±)-3,7-Dimethyl-1,6-octadien-3-ol. In some aspects, the essential oil further comprises from 10 to 18% w/w (±)-3,7-Dimethyl-1,6-octadien-3-ol. In some aspects, the essential oil further comprises from 10 to 17% w/w (±)-3,7-Dimethyl-1,6-octadien-3-ol. In some aspects, the essential oil further comprises from 10 to 16% w/w (±)-3,7-Dimethyl-1,6-octadien-3-ol. In some aspects, the essential oil further comprises from 10 to 15% w/w (±)-3,7-Dimethyl-1,6-octadien-3-ol. In some aspects, the essential oil further comprises from 10 to 14% w/w (±)-3,7-Dimethyl-1,6-octadien-3-ol. In some aspects, the essential oil further comprises from 10 to 13% w/w (±)-3,7-Dimethyl-1,6-octadien-3-ol. In some aspects, the essential oil further comprises from 10 to 12% w/w (±)-3,7-Dimethyl-1,6-octadien-3-ol. In some aspects, the essential oil further comprises from 10 to 11% w/w (±)-3,7-Dimethyl-1,6-octadien-3-ol.

In some aspects, the essential oil further comprises from 11 to 20% w/w (±)-3,7-Dimethyl-1,6-octadien-3-ol. In some aspects, the essential oil further comprises from 12 to 20% w/w (±)-3,7-Dimethyl-1,6-octadien-3-ol. In some aspects, the essential oil further comprises from 13 to 20% w/w (±)-3,7-Dimethyl-1,6-octadien-3-ol. In some aspects, the essential oil further comprises from 14 to 20% w/w (±)-3,7-Dimethyl-1,6-octadien-3-ol. In some aspects, the essential oil further comprises from 15 to 20% w/w (±)-3,7-Dimethyl-1,6-octadien-3-ol. In some aspects, the essential oil further comprises from 16 to 20% w/w (±)-3,7-Dimethyl-1,6-octadien-3-ol. In some aspects, the essential oil further comprises from 17 to 20% w/w (±)-3,7-Dimethyl-1,6-octadien-3-ol. In some aspects, the essential oil further comprises from 18 to 20% w/w (±)-3,7-Dimethyl-1,6-octadien-3-ol. In some aspects, the essential oil further comprises from 19 to 20% w/w (±)-3,7-Dimethyl-1,6-octadien-3-ol.

In some aspects, the essential oil further comprises at least 5% w/w (±)-3,7-Dimethyl-1,6-octadien-3-ol.

In some aspects, the essential oil further comprises at least 16% w/w (±)-3,7-Dimethyl-1,6-octadien-3-ol.

In some aspects, the essential oil further comprises 10, or 11, or 12, or 13, or 14, or 15, or 16, or 17, or 18, or 19, or 20% w/w (±)-3,7-Dimethyl-1,6-octadien-3-ol.

In some aspects, the essential oil further comprises from 20 to 70% w/w benzyl acetate. In some aspects, the essential oil further comprises from 20 to 65% w/w benzyl acetate. In some aspects, the essential oil further comprises from 20 to 60% w/w benzyl acetate. In some aspects, the essential oil further comprises from 20 to 55% w/w benzyl acetate. In some aspects, the essential oil further comprises from 20 to 50% w/w benzyl acetate. In some aspects, the essential oil further comprises from 20 to 45% w/w benzyl acetate. In some aspects, the essential oil further comprises from 20 to 40% w/w benzyl acetate. In some aspects, the essential oil further comprises from 20 to 35% w/w benzyl acetate. In some aspects, the essential oil further comprises from 20 to 30% w/w benzyl acetate. In some aspects, the essential oil further comprises from 20 to 25% w/w benzyl acetate.

In some aspects, the essential oil further comprises from 25 to 70% w/w benzyl acetate. In some aspects, the essential oil further comprises from 30 to 70% w/w benzyl acetate. In some aspects, the essential oil further comprises from 35 to 70% w/w benzyl acetate. In some aspects, the essential oil further comprises from 40 to 70% w/w benzyl acetate. In some aspects, the essential oil further comprises from 45 to 70% w/w benzyl acetate. In some aspects, the essential oil further comprises from 50 to 70% w/w benzyl acetate. In some aspects, the essential oil further comprises from 55 to 70% w/w benzyl acetate. In some aspects, the essential oil further comprises from 60 to 70% w/w benzyl acetate. In some aspects, the essential oil further comprises from 65 to 70% w/w benzyl acetate.

In some aspects, the essential oil further comprises from 40 to 65% w/w benzyl acetate. In some aspects, the essential oil further comprises from 40 to 64% w/w benzyl acetate. In some aspects, the essential oil further comprises from 40 to 63% w/w benzyl acetate. In some aspects, the essential oil further comprises from 40 to 62% w/w benzyl acetate. In some aspects, the essential oil further comprises from 40 to 61% w/w benzyl acetate. In some aspects, the essential oil further comprises from 40 to 60% w/w benzyl acetate. In some aspects, the essential oil further comprises from 40 to 59% w/w benzyl acetate. In some aspects, the essential oil further comprises from 40 to 58% w/w benzyl acetate. In some aspects, the essential oil further comprises from 40 to 57% w/w benzyl acetate. In some aspects, the essential oil further comprises from 40 to 56% w/w benzyl acetate. In some aspects, the essential oil further comprises from 40 to 55% w/w benzyl acetate. In some aspects, the essential oil further comprises from 40 to 54% w/w benzyl acetate. In some aspects, the essential oil further comprises from 40 to 53% w/w benzyl acetate. In some aspects, the essential oil further comprises from 40 to 52% w/w benzyl acetate. In some aspects, the essential oil further comprises from 40 to 51% w/w benzyl acetate. In some aspects, the essential oil further comprises from 40 to 50% w/w benzyl acetate. In some aspects, the essential oil further comprises from 40 to 49% w/w benzyl acetate. In some aspects, the essential oil further comprises from 40 to 48% w/w benzyl acetate. In some aspects, the essential oil further comprises from 40 to 47% w/w benzyl acetate. In some aspects, the essential oil further comprises from 40 to 46% w/w benzyl acetate. In some aspects, the essential oil further comprises from 40 to 45% w/w benzyl acetate. In some aspects, the essential oil further comprises from 40 to 44% w/w benzyl acetate. In some aspects, the essential oil further comprises from 40 to 43% w/w benzyl acetate. In some aspects, the essential oil further comprises from 40 to 42% w/w benzyl acetate. In some aspects, the essential oil further comprises from 40 to 41% w/w benzyl acetate.

In some aspects, the essential oil further comprises from 41 to 65% w/w benzyl acetate. In some aspects, the essential oil further comprises from 42 to 65% w/w benzyl acetate. In some aspects, the essential oil further comprises from 43 to 65% w/w benzyl acetate. In some aspects, the essential oil further comprises from 44 to 65% w/w benzyl acetate. In some aspects, the essential oil further comprises from 45 to 65% w/w benzyl acetate. In some aspects, the essential oil further comprises from 46 to 65% w/w benzyl acetate. In some aspects, the essential oil further comprises from 47 to 65% w/w benzyl acetate. In some aspects, the essential oil further comprises from 48 to 65% w/w benzyl acetate. In some aspects, the essential oil further comprises from 49 to 65% w/w benzyl acetate. In some aspects, the essential oil further comprises from 50 to 65% w/w benzyl acetate. In some aspects, the essential oil further comprises from 51 to 65% w/w benzyl acetate. In some aspects, the essential oil further comprises from 52 to 65% w/w benzyl acetate. In some aspects, the essential oil further comprises from 53 to 65% w/w benzyl acetate. In some aspects, the essential oil further comprises from 54 to 65% w/w benzyl acetate. In some aspects, the essential oil further comprises from 55 to 65% w/w benzyl acetate. In some aspects, the essential oil further comprises from 56 to 65% w/w benzyl acetate. In some aspects, the essential oil further comprises from 57 to 65% w/w benzyl acetate. In some aspects, the essential oil further comprises from 58 to 65% w/w benzyl acetate. In some aspects, the essential oil further comprises from 59 to 65% w/w benzyl acetate. In some aspects, the essential oil further comprises from 60 to 65% w/w benzyl acetate. In some aspects, the essential oil further comprises from 61 to 65% w/w benzyl acetate. In some aspects, the essential oil further comprises from 62 to 65% w/w benzyl acetate. In some aspects, the essential oil further comprises from 63 to 65% w/w benzyl acetate. In some aspects, the essential oil further comprises from 64 to 65% w/w benzyl acetate.

In some aspects, the essential oil further comprises at least 20% w/w benzyl acetate.

In some aspects, the essential oil further comprises 20, or 21, or 22, or 23, or 24, or 25, or 26, or 27, or 28, or 29, or 30, or 31, or 32, or 33, or 34, or 35, or 36, or 37, or 38, or 39, or 40, or 41, or 42, or 43, or 44, or 45, or 46, or 47, or 48, or 49, or 50, or 51, or 52, or 53, or 54, or 55, or 56, or 57, or 58, or 59, or 60, or 61, or 62, or 63, or 64, or 65 w/ benzyl acetate.

Molecules that may introduce an artifact to the jasmine flower scent include benzyl benzoate. In some aspects, the levels benzyl benzoate are lower compared to essential oils derived from *Jasminium grandiflorum,* using conventional methods. Accordingly, the essential oil smells more like fresh jasmine flowers, compared to essential oils having higher levels of benzyl benzoate.

In some aspects, the essential oil further comprises no more than 7% w/w benzyl benzoate.

In some aspects, the essential oil further comprises from 1 to 6.5% w/w benzyl benzoate. In some aspects, the essential oil further comprises from 1 to 6.4% w/w benzyl benzoate. In some aspects, the essential oil further comprises from 1 to 6.3% w/w benzyl benzoate. In some aspects, the essential oil further comprises from 1 to 6.2% w/w benzyl benzoate. In some aspects, the essential oil further comprises from 1 to 6.1% w/w benzyl benzoate. In some aspects, the essential oil further comprises from 1 to 6% w/w benzyl benzoate. In some aspects, the essential oil further comprises from 1 to 5.9% w/w benzyl benzoate. In some aspects, the essential oil further comprises from 1 to 5.8% w/w benzyl benzoate. In some aspects, the essential oil further comprises from 1 to 5.7% w/w benzyl benzoate. In some aspects, the essential oil further comprises from 1 to 5.6% w/w benzyl benzoate. In some aspects, the essential oil further comprises from 1 to 5.5% w/w benzyl benzoate. In some aspects, the essential oil further comprises from 1 to 5.4% w/w benzyl benzoate. In some aspects, the essential oil further comprises from 1 to 5.3% w/w benzyl benzoate. In some aspects, the essential oil further comprises from 1 to 5.2% w/w benzyl benzoate. In some aspects, the essential oil further comprises from 1 to 5.1% w/w benzyl benzoate. In some aspects, the essential oil further comprises from 1 to 5% w/w benzyl benzoate. In some aspects, the essential oil further comprises from 1 to 4.9% w/w benzyl benzoate. In some aspects, the essential oil further comprises from 1 to 4.8% w/w benzyl benzoate. In some aspects, the essential oil further comprises from 1 to 4.7% w/w benzyl benzoate. In some aspects, the essential oil further comprises from 1 to 4.6% w/w benzyl benzoate. In some aspects, the essential oil further comprises from 1 to 4.5% w/w benzyl benzoate. In some aspects, the essential oil further comprises from 1 to 4.4% w/w benzyl benzoate. In some aspects, the essential oil further comprises from 1 to 4.3% w/w benzyl benzoate. In some aspects, the essential oil further comprises from 1 to 4.2% w/w benzyl benzoate. In some aspects, the essential oil further comprises from 1 to 4.1% w/w benzyl benzoate. In some aspects, the essential oil further comprises from 1 to 4% w/w benzyl benzoate. In some aspects, the essential oil further comprises from 1 to 3.9% w/w benzyl benzoate. In some aspects, the essential oil further comprises from 1 to 3.8% w/w benzyl benzoate. In some aspects, the essential oil further comprises from 1 to 3.7% w/w benzyl benzoate. In some aspects, the essential oil further comprises from 1 to 3.6% w/w benzyl benzoate. In some aspects, the essential oil further comprises from 1 to 3.5% w/w benzyl benzoate. In some aspects, the essential oil further comprises from 1 to 3.4% w/w benzyl benzoate. In some aspects, the essential oil further comprises from 1 to 3.3% w/w benzyl benzoate. In some aspects, the essential oil further comprises from 1 to 3.2% w/w benzyl benzoate. In some aspects, the essential oil further comprises from 1 to 3.1% w/w benzyl benzoate. In some aspects, the essential oil further comprises from 1 to 3% w/w benzyl benzoate. In some aspects, the essential oil further comprises from 1 to 2.9% w/w benzyl benzoate. In some aspects, the essential oil further comprises from 1 to 2.8% w/w benzyl benzoate. In some aspects, the essential oil further comprises from 1 to 2.7% w/w benzyl benzoate. In some aspects, the essential oil further comprises from 1 to 2.6% w/w benzyl benzoate. In some aspects, the essential oil further comprises from 1 to 2.5% w/w benzyl benzoate. In some aspects, the essential oil further comprises from 1 to 2.4% w/w benzyl benzoate. In some aspects, the essential oil further comprises from 1 to 2.3% w/w benzyl benzoate. In some aspects, the essential oil further comprises from 1 to 2.2% w/w benzyl benzoate. In some aspects, the essential oil further comprises from 1 to 2.1% w/w benzyl benzoate. In some aspects, the essential oil further comprises from 1 to 2% w/w benzyl benzoate. In some aspects, the essential oil further comprises from 1 to 1.9% w/w benzyl benzoate. In some aspects, the essential oil further comprises from 1 to 1.8% w/w benzyl benzoate. In some aspects, the essential oil further comprises from 1 to 1.7% w/w benzyl benzoate. In some aspects, the essential oil further comprises from 1 to 1.6% w/w benzyl benzoate. In some aspects, the essential oil further comprises from 1 to 1.5% w/w benzyl benzoate. In some aspects, the essential oil further comprises from 1 to 1.4% w/w benzyl benzoate. In some aspects, the essential oil further comprises from 1 to 1.3% w/w benzyl benzoate. In some aspects, the essential oil further comprises from 1 to 1.2% w/w benzyl benzoate. In some aspects, the essential oil further comprises from 1 to 1.1% w/w benzyl benzoate.

In some aspects, the essential oil further comprises from 1 to 6.5% w/w benzyl benzoate. In some aspects, the essential oil further comprises from 1.1 to 6.5% w/w benzyl benzoate. In some aspects, the essential oil further comprises from 1.2 to 6.5% w/w benzyl benzoate. In some aspects, the essential oil further comprises from 1.3 to 6.5% w/w benzyl benzoate. In some aspects, the essential oil further comprises from 1.4 to 6.5% w/w benzyl benzoate. In some aspects, the essential oil further comprises from 1.5 to 6.5% w/w benzyl benzoate. In some aspects, the essential oil further comprises from 1.6 to 6.5% w/w benzyl benzoate. In some aspects, the essential oil further comprises from 1.7 to 6.5% w/w benzyl benzoate. In some aspects, the essential oil further comprises from 1.8 to 6.5% w/w benzyl benzoate. In some aspects, the essential oil further comprises from 1.9 to 6.5% w/w benzyl benzoate. In some aspects, the essential oil further comprises from 2 to 6.5% w/w benzyl benzoate. In some aspects, the essential oil further comprises from 2.1 to 6.5% w/w benzyl benzoate. In some aspects, the essential oil further comprises from 2.2 to 6.5% w/w benzyl benzoate. In some aspects, the essential oil further comprises from 2.3 to 6.5% w/w benzyl benzoate. In some aspects, the essential oil further comprises from 2.4 to 6.5% w/w benzyl benzoate. In some aspects, the essential oil further comprises from 2.5 to 6.5% w/w benzyl benzoate. In some aspects, the essential oil further comprises from 2.6 to 6.5% w/w benzyl benzoate. In some aspects, the essential oil further comprises from 2.7 to 6.5% w/w benzyl benzoate. In some aspects, the essential oil further comprises from 2.8 to 6.5% w/w benzyl benzoate. In some aspects, the essential oil further comprises from 2.9 to 6.5% w/w benzyl benzoate. In some aspects, the essential oil further comprises from 3 to 6.5% w/w benzyl benzoate. In some aspects, the essential oil further comprises from 3.1 to 6.5% w/w benzyl benzoate. In some aspects, the essential oil further comprises from 3.2 to 6.5% w/w benzyl benzoate. In some aspects, the essential oil further comprises from 3.3 to 6.5% w/w benzyl benzoate. In some aspects, the essential oil further comprises from 3.4 to 6.5% w/w benzyl benzoate. In some aspects, the essential oil further comprises from 3.5 to 6.5% w/w benzyl benzoate. In some aspects, the essential oil further comprises from 3.6 to 6.5% w/w benzyl benzoate. In some aspects, the essential oil further comprises from 3.7 to 6.5% w/w benzyl benzoate. In some aspects, the essential oil further comprises from 3.8 to 6.5% w/w benzyl benzoate. In some aspects, the essential oil further comprises from 3.9 to 6.5% w/w benzyl benzoate. In some aspects, the essential oil further comprises from 4 to 6.5% w/w benzyl benzoate. In some aspects, the essential oil further comprises from 4.1 to 6.5% w/w benzyl benzoate. In some aspects, the essential oil further comprises from 4.2 to 6.5% w/w benzyl benzoate. In some aspects, the essential oil further comprises from 4.3 to 6.5% w/w benzyl benzoate. In some aspects, the essential oil further comprises from 4.4 to 6.5% w/w benzyl benzoate. In some aspects, the essential oil further comprises from 4.5 to 6.5% w/w benzyl benzoate. In some aspects, the essential oil further comprises from 4.6 to 6.5% w/w benzyl benzoate. In some aspects, the essential oil further comprises from 4.7 to 6.5% w/w benzyl benzoate. In some aspects, the essential oil further comprises from 4.8 to 6.5% w/w benzyl benzoate. In some aspects, the essential oil further comprises from 4.9 to 6.5% w/w benzyl benzoate. In some aspects, the essential oil further comprises from 5 to 6.5% w/w benzyl benzoate. In some aspects, the essential oil further comprises from 5.1 to 6.5% w/w benzyl benzoate. In some aspects, the essential oil further comprises from 5.2 to 6.5% w/w benzyl benzoate. In some aspects, the essential oil further comprises from 5.3 to 6.5% w/w benzyl benzoate. In some aspects, the essential oil further comprises from 5.4 to 6.5% w/w benzyl benzoate. In some aspects, the essential oil further comprises from 5.5 to 6.5% w/w benzyl benzoate. In some aspects, the essential oil further comprises from 5.6 to 6.5% w/w benzyl benzoate. In some aspects, the essential oil further comprises from 5.7 to 6.5% w/w benzyl benzoate. In some aspects, the essential oil further comprises from 5.8 to 6.5% w/w benzyl benzoate. In some aspects, the essential oil further comprises from 5.9 to 6.5% w/w benzyl benzoate. In some aspects, the essential oil further comprises from 6 to 6.5% w/w benzyl benzoate. In some aspects, the essential oil further comprises from 6.1 to 6.5% w/w benzyl benzoate. In some aspects, the essential oil further comprises from 6.2 to 6.5% w/w benzyl benzoate. In some aspects, the essential oil further comprises from 6.3 to 6.5% w/w benzyl benzoate. In some aspects, the essential oil further comprises from 6.4 to 6.5% w/w benzyl benzoate.

In some aspects, the essential oil further comprises 1, or 1.1, or 1.2, or 1.3, or 1.4, or 1.5, or 1.6, or 1.7, or 1.8, or 1.9, or 2, or 2.1, or 2.2, or 2.3, or 2.4, or 2.5, or 2.6, or 2.7, or 2.8, or 2.9, or 3, or 3.1, or 3.2, or 3.3, or 3.4, or 3.5, or 3.6, or 3.7, or 3.8, or 3.9, or 4, or 4.1, or 4.2, or 4.3, or 4.4, or 4.5, or 4.6, or 4.7, or 4.8, or 4.9, or 5, or 5.1, or 5.2, or 5.3, or 5.4, or 5.5, or 5.6, or 5.7, or 5.8, or 5.9, or 6, or 6.1, or 6.2, or 6.3, or 6.4, or 6.5% w/w benzyl benzoate.

In some aspects, the essential oil comprises from 7 to 11% w/w (z)-jasmone, from 10 to 17% w/w (±)-3,7-Dimethyl-1,6-octadien-3-ol, from 40 to 62% w/w benzyl acetate, and from 1 to 7.1% w/w benzyl benzoate.

In some aspects, the essential oil comprises any one of Microwave Extract 1, Microwave Extract 2, or Microwave Extract 3, disclosed in Table 1.

In some aspects, the essential oil comprises the compounds, at the amounts disclosed in any one of Microwave Extract 1, Microwave Extract 2, or Microwave Extract 3, disclosed in Table 1.

Essential Oil Derived from *Piper nigrum:* One aspect presented herein provides an essential oil extracted from *Piper nigrum,* wherein the essential oil comprises at least 7% w/w sabinine.

In some aspects, the essential oil comprises from 9 to 15% w/w sabinine. In some aspects, the essential oil comprises from 9 to 15% w/w sabinine. In some aspects, the essential oil comprises from 10 to 15% w/w sabinine. In some aspects, the essential oil comprises from 11 to 15% w/w sabinine. In some aspects, the essential oil comprises from 12 to 15% w/w sabinine. In some aspects, the essential oil comprises from 13 to 15% w/w sabinine. In some aspects, the essential oil comprises from 14 to 15% w/w sabinine.

In some aspects, the essential oil comprises from 9 to 14% w/w sabinine. In some aspects, the essential oil comprises from 9 to 13% w/w sabinine. In some aspects, the essential oil comprises from 9 to 12% w/w sabinine. In some aspects, the essential oil comprises from 9 to 11% w/w sabinine. In some aspects, the essential oil comprises from 9 to 10% w/w sabinine.

In some aspects, the essential oil comprises 9, or 10, or 11, or 12, or 13, or 14, or 15% w/w sabinine.

In some aspects, the essential oil further comprises from 12 to 16% w/w β-pinene. In some aspects, the essential oil further comprises from 13 to 16% w/w β-pinene. In some aspects, the essential oil further comprises from 14 to 16% w/w β-pinene. In some aspects, the essential oil further comprises from 15 to 16% w/w β-pinene.

In some aspects, the essential oil further comprises from 12 to 15% w/w β-pinene. In some aspects, the essential oil further comprises from 12 to 14% w/w β-pinene. In some aspects, the essential oil further comprises from 12 to 13% w/w β-pinene.

In some aspects, the essential oil further comprises 12, or 13, or 14, or 15, or 16% w/w β-pinene.

In some aspects, the essential oil further comprises from 20 to 30% w/w limonene. In some aspects, the essential oil further comprises from 21 to 30% w/w limonene. In some aspects, the essential oil further comprises from 22 to 30% w/w limonene. In some aspects, the essential oil further comprises from 23 to 30% w/w limonene. In some aspects, the essential oil further comprises from 24 to 30% w/w limonene. In some aspects, the essential oil further comprises from 25 to 30% w/w limonene. In some aspects, the essential oil further comprises from 26 to 30% w/w limonene. In some aspects, the essential oil further comprises from 27 to 30% w/w limonene. In some aspects, the essential oil further comprises from 28 to 30% w/w limonene. In some aspects, the essential oil further comprises from 29 to 30% w/w limonene.

In some aspects, the essential oil further comprises from 20 to 29% w/w limonene. In some aspects, the essential oil further comprises from 20 to 28% w/w limonene. In some aspects, the essential oil further comprises from 20 to 27% w/w limonene. In some aspects, the essential oil further comprises from 20 to 26% w/w limonene. In some aspects, the essential oil further comprises from 20 to 25% w/w limonene. In some aspects, the essential oil further comprises from 20 to 24% w/w limonene. In some aspects, the essential oil further comprises from 20 to 23% w/w limonene. In some aspects, the essential oil further comprises from 20 to 22% w/w limonene. In some aspects, the essential oil further comprises from 20 to 21% w/w limonene.

In some aspects, the essential oil further comprises 20, or 21, or 22, or 23, or 24, or 25, or 26, or 27, or 28, or 29, or 30% w/w limonene.

In some aspects, the essential oil further comprises from 7 to 12% w/w beta-caryophyllene. In some aspects, the essential oil further comprises from 8 to 12% w/w beta-caryophyllene. In some aspects, the essential oil further comprises from 9 to 12% w/w beta-caryophyllene. In some aspects, the essential oil further comprises from 10 to 12% w/w beta-caryophyllene. In some aspects, the essential oil further comprises from 11 to 12% w/w beta-caryophyllene.

In some aspects, the essential oil further comprises from 7 to 11% w/w beta-caryophyllene. In some aspects, the essential oil further comprises from 7 to 10% w/w beta-caryophyllene. In some aspects, the essential oil further comprises from 7 to 9% w/w beta-caryophyllene. In some aspects, the essential oil further comprises from 7 to 8% w/w beta-caryophyllene.

In some aspects, the essential oil further comprises 7, or 8, or 9, or 10, or 11, or 12% w/w beta-caryophyllene.

In some aspects, the essential oil further comprises less than 3% w/w piperine.

In some aspects, the essential oil comprises the compounds, at the amounts disclosed in any one of Microwave Extract 1, or Microwave Extract 2 disclosed in Table 2.

Essential Oil Derived from Ginger Root: One aspect presented herein provides an essential oil extracted from ginger root, wherein the essential oil comprises at least 13% w/w eucalyptol.

In some aspects, the essential oil comprises from 13 to 15% w/w eucalyptol. In some aspects, the essential oil comprises from 13 to 14% w/w eucalyptol.

In some aspects, the essential oil comprises 13, or 14, or 15% w/w eucalyptol.

In some aspects, the essential oil comprises from 2 to 6% w/w 6-methyl-5-hepten-2-one. In some aspects, the essential oil comprises from 3 to 6% w/w 6-methyl-5-hepten-2-one. In some aspects, the essential oil comprises from 4 to 6% w/w 6-methyl-5-hepten-2-one. In some aspects, the essential oil comprises from 5 to 6% w/w 6-methyl-5-hepten-2-one.

In some aspects, the essential oil comprises from 2 to 5% w/w 6-methyl-5-hepten-2-one. In some aspects, the essential oil comprises from 2 to 4% w/w 6-methyl-5-hepten-2-one. In some aspects, the essential oil comprises from 2 to 3% w/w 6-methyl-5-hepten-2-one.

In some aspects, the essential oil comprises 2, or 3, or 4, or 5, or 6% w/w 6-methyl-5-hepten-2-one.

In some aspects, the essential oil comprises from 19 to 25% w/w neral. In some aspects, the essential oil comprises from 20 to 25% w/w neral. In some aspects, the essential oil comprises from 21 to 25% w/w neral. In some aspects, the essential oil comprises from 22 to 25% w/w neral. In some aspects, the essential oil comprises from 23 to 25% w/w neral. In some aspects, the essential oil comprises from 24 to 25% w/w neral.

In some aspects, the essential oil comprises from 19 to 24% w/w neral. In some aspects, the essential oil comprises from 19 to 23% w/w neral. In some aspects, the essential oil comprises from 19 to 22% w/w neral. In some aspects, the essential oil comprises from 19 to 21% w/w neral. In some aspects, the essential oil comprises from 19 to 20% w/w neral.

In some aspects, the essential oil comprises 19, or 20, or 21, or 22, or 23, or 24, or 25% w/w neral.

In some aspects, the essential oil comprises from 26 to 29% w/w geranial. In some aspects, the essential oil comprises from 27 to 29% w/w geranial. In some aspects, the essential oil comprises from 28 to 29% w/w geranial.

In some aspects, the essential oil comprises from 26 to 28% w/w geranial. In some aspects, the essential oil comprises from 26 to 27% w/w geranial.

In some aspects, the essential oil comprises 26, or 27, or 28, or 29% w/w geranial.

In some aspects, the essential oil comprises greater than 0.1% w/w 2-heptanone.

In some aspects, the essential oil comprises greater than 0.2% w/w nerol.

In some aspects, the essential oil comprises less than 1% w/w geraniol.

In some aspects, the essential oil comprises less than 18.5% w/w zingiberene.

In some aspects, the essential oil comprises the compounds, at the amounts disclosed in any one of Microwave Extract 1, or Microwave Extract 2 disclosed in Table 5.

Extract Derived from Pears: One aspect presented herein provides an extract from pears, wherein the extract comprises at least 0.1% w/w hexyl acetate.

In some aspects, the extract comprises from 0.1 to 6% w/w hexyl acetate. In some aspects, the extract comprises from 0.2 to 6% w/w hexyl acetate. In some aspects, the extract comprises from 0.3 to 6% w/w hexyl acetate. In some aspects, the extract comprises from 0.4 to 6% w/w hexyl acetate. In some aspects, the extract comprises from 0.5 to 6% w/w hexyl acetate. In some aspects, the extract comprises from 0.6 to 6% w/w hexyl acetate. In some aspects, the extract comprises from 0.7 to 6% w/w hexyl acetate. In some aspects, the extract comprises from 0.8 to 6% w/w hexyl acetate. In some aspects, the extract comprises from 0.9 to 6% w/w hexyl acetate. In some aspects, the extract comprises from 1 to 6% w/w hexyl acetate. In some aspects, the extract comprises from 1.1 to 6% w/w hexyl acetate. In some aspects, the extract comprises from 1.2 to 6% w/w hexyl acetate. In some aspects, the extract comprises from 1.3 to 6% w/w hexyl acetate. In some aspects, the extract comprises from 1.4 to 6% w/w hexyl acetate. In some aspects, the extract comprises from 1.5 to 6% w/w hexyl acetate. In some aspects, the extract comprises from 1.6 to 6% w/w hexyl acetate. In some aspects, the extract comprises from 1.7 to 6% w/w hexyl acetate. In some aspects, the extract comprises from 1.8 to 6% w/w hexyl acetate. In some aspects, the extract comprises from 1.9 to 6% w/w hexyl acetate. In some aspects, the extract comprises from 2 to 6% w/w hexyl acetate. In some aspects, the extract comprises from 2.1 to 6% w/w hexyl acetate. In some aspects, the extract comprises from 2.2 to 6% w/w hexyl acetate. In some aspects, the extract comprises from 2.3 to 6% w/w hexyl acetate. In some aspects, the extract comprises from 2.4 to 6% w/w hexyl acetate. In some aspects, the extract comprises from 2.5 to 6% w/w hexyl acetate. In some aspects, the extract comprises from 2.6 to 6% w/w hexyl acetate. In some aspects, the extract comprises from 2.7 to 6% w/w hexyl acetate. In some aspects, the extract comprises from 2.8 to 6% w/w hexyl acetate. In some aspects, the extract comprises from 2.9 to 6% w/w hexyl acetate. In some aspects, the extract comprises from 3 to 6% w/w hexyl acetate. In some aspects, the extract comprises from 3.1 to 6% w/w hexyl acetate. In some aspects, the extract comprises from 3.2 to 6% w/w hexyl acetate. In some aspects, the extract comprises from 3.3 to 6% w/w hexyl acetate. In some aspects, the extract comprises from 3.4 to 6% w/w hexyl acetate. In some aspects, the extract comprises from 3.5 to 6% w/w hexyl acetate. In some aspects, the extract comprises from 3.6 to 6% w/w hexyl acetate. In some aspects, the extract comprises from 3.7 to 6% w/w hexyl acetate. In some aspects, the extract comprises from 3.8 to 6% w/w hexyl acetate. In some aspects, the extract comprises from 3.9 to 6% w/w hexyl acetate. In some aspects, the extract comprises from 4 to 6% w/w hexyl acetate. In some aspects, the extract comprises from 4.1 to 6% w/w hexyl acetate. In some aspects, the extract comprises from 4.2 to 6% w/w hexyl acetate. In some aspects, the extract comprises from 4.3 to 6% w/w hexyl acetate. In some aspects, the extract comprises from 4.4 to 6% w/w hexyl acetate. In some aspects, the extract comprises from 4.5 to 6% w/w hexyl acetate. In some aspects, the extract comprises from 4.6 to 6% w/w hexyl acetate. In some aspects, the extract comprises from 4.7 to 6% w/w hexyl acetate. In some aspects, the extract comprises from 4.8 to 6% w/w hexyl acetate. In some aspects, the extract comprises from 4.9 to 6% w/w hexyl acetate. In some aspects, the extract comprises from 5 to 6% w/w hexyl acetate. In some aspects, the extract comprises from 5.1 to 6% w/w hexyl acetate. In some aspects, the extract comprises from 5.2 to 6% w/w hexyl acetate. In some aspects, the extract comprises from 5.3 to 6% w/w hexyl acetate. In some aspects, the extract comprises from 5.4 to 6% w/w hexyl acetate. In some aspects, the extract comprises from 5.5 to 6% w/w hexyl acetate. In some aspects, the extract comprises from 5.6 to 6% w/w hexyl acetate. In some aspects, the extract comprises from 5.7 to 6% w/w hexyl acetate. In some aspects, the extract comprises from 5.8 to 6% w/w hexyl acetate. In some aspects, the extract comprises from 5.9 to 6% w/w hexyl acetate.

In some aspects, the extract comprises from 0.1 to 5.9% w/w hexyl acetate. In some aspects, the extract comprises from 0.1 to 5.8% w/w hexyl acetate. In some aspects, the extract comprises from 0.1 to 5.7% w/w hexyl acetate. In some aspects, the extract comprises from 0.1 to 5.6% w/w hexyl acetate. In some aspects, the extract comprises from 0.1 to 5.5% w/w hexyl acetate. In some aspects, the extract comprises from 0.1 to 5.4% w/w hexyl acetate. In some aspects, the extract comprises from 0.1 to 5.3% w/w hexyl acetate. In some aspects, the extract comprises from 0.1 to 5.2% w/w hexyl acetate. In some aspects, the extract comprises from 0.1 to 5.1% w/w hexyl acetate. In some aspects, the extract comprises from 0.1 to 5% w/w hexyl acetate. In some aspects, the extract comprises from 0.1 to 4.9% w/w hexyl acetate. In some aspects, the extract comprises from 0.1 to 4.8% w/w hexyl acetate. In some aspects, the extract comprises from 0.1 to 4.7% w/w hexyl acetate. In some aspects, the extract comprises from 0.1 to 4.6% w/w hexyl acetate. In some aspects, the extract comprises from 0.1 to 4.5% w/w hexyl acetate. In some aspects, the extract comprises from 0.1 to 4.4% w/w hexyl acetate. In some aspects, the extract comprises from 0.1 to 4.3% w/w hexyl acetate. In some aspects, the extract comprises from 0.1 to 4.2% w/w hexyl acetate. In some aspects, the extract comprises from 0.1 to 4.1% w/w hexyl acetate. In some aspects, the extract comprises from 0.1 to 4% w/w hexyl acetate. In some aspects, the extract comprises from 0.1 to 3.9% w/w hexyl acetate. In some aspects, the extract comprises from 0.1 to 3.8% w/w hexyl acetate. In some aspects, the extract comprises from 0.1 to 3.7% w/w hexyl acetate. In some aspects, the extract comprises from 0.1 to 3.6% w/w hexyl acetate. In some aspects, the extract comprises from 0.1 to 3.5% w/w hexyl acetate. In some aspects, the extract comprises from 0.1 to 3.4% w/w hexyl acetate. In some aspects, the extract comprises from 0.1 to 3.3% w/w hexyl acetate. In some aspects, the extract comprises from 0.1 to 3.2% w/w hexyl acetate. In some aspects, the extract comprises from 0.1 to 3.1% w/w hexyl acetate. In some aspects, the extract comprises from 0.1 to 3% w/w hexyl acetate. In some aspects, the extract comprises from 0.1 to 2.9% w/w hexyl acetate. In some aspects, the extract comprises from 0.1 to 2.8% w/w hexyl acetate. In some aspects, the extract comprises from 0.1 to 2.7% w/w hexyl acetate. In some aspects, the extract comprises from 0.1 to 2.6% w/w hexyl acetate. In some aspects, the extract comprises from 0.1 to 2.5% w/w hexyl acetate. In some aspects, the extract comprises from 0.1 to 2.4% w/w hexyl acetate. In some aspects, the extract comprises from 0.1 to 2.3% w/w hexyl acetate. In some aspects, the extract comprises from 0.1 to 2.2% w/w hexyl acetate. In some aspects, the extract comprises from 0.1 to 2.1% w/w hexyl acetate. In some aspects, the extract comprises from 0.1 to 2% w/w hexyl acetate. In some aspects, the extract comprises from 0.1 to 1.9% w/w hexyl acetate. In some aspects, the extract comprises from 0.1 to 1.8% w/w hexyl acetate. In some aspects, the extract comprises from 0.1 to 1.7% w/w hexyl acetate. In some aspects, the extract comprises from 0.1 to 1.6% w/w hexyl acetate. In some aspects, the extract comprises from 0.1 to 1.5% w/w hexyl acetate. In some aspects, the extract comprises from 0.1 to 1.4% w/w hexyl acetate. In some aspects, the extract comprises from 0.1 to 1.3% w/w hexyl acetate. In some aspects, the extract comprises from 0.1 to 1.2% w/w hexyl acetate. In some aspects, the extract comprises from 0.1 to 1.1% w/w hexyl acetate. In some aspects, the extract comprises from 0.1 to 1% w/w hexyl acetate. In some aspects, the extract comprises from 0.1 to 0.9% w/w hexyl acetate. In some aspects, the extract comprises from 0.1 to 0.8% w/w hexyl acetate. In some aspects, the extract comprises from 0.1 to 0.7% w/w hexyl acetate. In some aspects, the extract comprises from 0.1 to 0.6% w/w hexyl acetate. In some aspects, the extract comprises from 0.1 to 0.5% w/w hexyl acetate. In some aspects, the extract comprises from 0.1 to 0.4% w/w hexyl acetate. In some aspects, the extract comprises from 0.1 to 0.3% w/w hexyl acetate. In some aspects, the extract comprises from 0.1 to 0.2% w/w hexyl acetate.

In some aspects, the extract comprises 0.1, or 0.2, or 0.3, or 0.4, or 0.5, or 0.6, or 0.7, or 0.8, or 0.9, or 1, or 1.1, or 1.2, or 1.3, or 1.4, or 1.5, or 1.6, or 1.7, or 1.8, or 1.9, or 2, or 2.1, or 2.2, or 2.3, or 2.4, or 2.5, or 2.6, or 2.7, or 2.8, or 2.9, or 3, or 3.1, or 3.2, or 3.3, or 3.4, or 3.5, or 3.6, or 3.7, or 3.8, or 3.9, or 4, or 4.1, or 4.2, or 4.3, or 4.4, or 4.5, or 4.6, or 4.7, or 4.8, or 4.9, or 5, or 5.1, or 5.2, or 5.3, or 5.4, or 5.5, or 5.6, or 5.7, or 5.8, or 5.9, or 6% w/w hexyl acetate.

In some aspects, the extract further comprises from 3 to 15% w/w acetol. In some aspects, the extract further comprises from 3 to 14% w/w acetol. In some aspects, the extract further comprises from 3 to 13% w/w acetol. In some aspects, the extract further comprises from 3 to 12% w/w acetol. In some aspects, the extract further comprises from 3 to 11% w/w acetol. In some aspects, the extract further comprises from 3 to 10% w/w acetol. In some aspects, the extract further comprises from 3 to 9% w/w acetol. In some aspects, the extract further comprises from 3 to 8% w/w acetol. In some aspects, the extract further comprises from 3 to 7% w/w acetol. In some aspects, the extract further comprises from 3 to 6% w/w acetol. In some aspects, the extract further comprises from 3 to 5% w/w acetol. In some aspects, the extract further comprises from 3 to 4% w/w acetol.

In some aspects, the extract further comprises from 4 to 15% w/w acetol. In some aspects, the extract further comprises from 5 to 15% w/w acetol. In some aspects, the extract further comprises from 6 to 15% w/w acetol. In some aspects, the extract further comprises from 7 to 15% w/w acetol. In some aspects, the extract further comprises from 8 to 15% w/w acetol. In some aspects, the extract further comprises from 9 to 15% w/w acetol. In some aspects, the extract further comprises from 10 to 15% w/w acetol. In some aspects, the extract further comprises from 11 to 15% w/w acetol. In some aspects, the extract further comprises from 12 to 15% w/w acetol. In some aspects, the extract further comprises from 13 to 15% w/w acetol. In some aspects, the extract further comprises from 14 to 15% w/w acetol.

In some aspects, the extract further comprises 3, or 4, or 5, or 6, or 7, or 8, or 9, or 10, or 11, or 12, or 13, or 14, or 15% w/w acetol.

In some aspects, the extract further comprises from 2 to 8% w/w acetic acid. In some aspects, the extract further comprises from 3 to 8% w/w acetic acid. In some aspects, the extract further comprises from 4 to 8% w/w acetic acid. In some aspects, the extract further comprises from 5 to 8% w/w acetic acid. In some aspects, the extract further comprises from 6 to 8% w/w acetic acid. In some aspects, the extract further comprises from 7 to 8% w/w acetic acid.

In some aspects, the extract further comprises from 2 to 7% w/w acetic acid. In some aspects, the extract further comprises from 2 to 6% w/w acetic acid. In some aspects, the extract further comprises from 2 to 5% w/w acetic acid. In some aspects, the extract further comprises from 2 to 4% w/w acetic acid. In some aspects, the extract further comprises from 2 to 3% w/w acetic acid.

In some aspects, the extract further comprises 2, or 3, or 4, or 5, or 6, or 7, or 8% w/w acetic acid.

In some aspects, the extract further comprises from 0.5 to 2% w/w furfural. In some aspects, the extract further comprises from 1 to 2% w/w furfural. In some aspects, the extract further comprises from 1.5 to 2% w/w furfural.

In some aspects, the extract further comprises from 0.5 to 1.5% w/w furfural. In some aspects, the extract further comprises from 0.5 to 1% w/w furfural.

In some aspects, the extract further comprises 0.5, or 1, or 1.5, or 2% w/w furfural.

In some aspects, the extract further comprises from 0.5 to 2% w/w furfural alcohol. In some aspects, the extract further comprises from 1 to 2% w/w furfural alcohol. In some aspects, the extract further comprises from 1.5 to 2% w/w furfural alcohol.

In some aspects, the extract further comprises from 0.5 to 1.5% w/w furfural alcohol.

In some aspects, the extract further comprises from 0.5 to 1% w/w furfural alcohol.

In some aspects, the extract further comprises 0.5, or 1, or 1.5, or 2% w/w furfural alcohol.

In some aspects, the extract further comprises from 0.2 to 2% w/w 2-methylbutyric acid. In some aspects, the extract further comprises from 0.4 to 2% w/w 2-methylbutyric acid. In some aspects, the extract further comprises from 0.6 to 2% w/w 2-methylbutyric acid. In some aspects, the extract further comprises from 0.8 to 2% w/w 2-methylbutyric acid. In some aspects, the extract further comprises from 1 to 2% w/w 2-methylbutyric acid. In some aspects, the extract further comprises from 1.2 to 2% w/w 2-methylbutyric acid. In some aspects, the extract further comprises from 1.4 to 2% w/w 2-methylbutyric acid. In some aspects, the extract further comprises from 1.6 to 2% w/w 2-methylbutyric acid. In some aspects, the extract further comprises from 1.8 to 2% w/w 2-methylbutyric acid.

In some aspects, the extract further comprises from 0.2 to 1.8% w/w 2-methylbutyric acid. In some aspects, the extract further comprises from 0.2 to 1.6% w/w 2-methylbutyric acid. In some aspects, the extract further comprises from 0.2 to 1.4% w/w 2-methylbutyric acid. In some aspects, the extract further comprises from 0.2 to 1.2% w/w 2-methylbutyric acid. In some aspects, the extract further comprises from 0.2 to 1% w/w 2-methylbutyric acid. In some aspects, the extract further comprises from 0.2 to 0.8% w/w 2-methylbutyric acid. In some aspects, the extract further comprises from 0.2 to 0.6% w/w 2-methylbutyric acid. In some aspects, the extract further comprises from 0.2 to 0.4% w/w 2-methylbutyric acid.

In some aspects, the extract further comprises 0.2, or 0.4, or 0.6, or 0.8, or 1, or 1.2, or 1.4, or 1.6, or 1.8, or 2% w/w 2-methylbutyric acid.

In some aspects, the extract further comprises from 6 to 46% w/w 1,3-dihydroxyacetone. In some aspects, the extract further comprises from 7 to 46% w/w 1,3-dihydroxyacetone. In some aspects, the extract further comprises from 8 to 46% w/w 1,3-dihydroxyacetone. In some aspects, the extract further comprises from 9 to 46% w/w 1,3-dihydroxyacetone. In some aspects, the extract further comprises from 10 to 46% w/w 1,3-dihydroxyacetone. In some aspects, the extract further comprises from 11 to 46% w/w 1,3-dihydroxyacetone. In some aspects, the extract further comprises from 12 to 46% w/w 1,3-dihydroxyacetone. In some aspects, the extract further comprises from 13 to 46% w/w 1,3-dihydroxyacetone. In some aspects, the extract further comprises from 14 to 46% w/w 1,3-dihydroxyacetone. In some aspects, the extract further comprises from 15 to 46% w/w 1,3-dihydroxyacetone. In some aspects, the extract further comprises from 16 to 46% w/w 1,3-dihydroxyacetone. In some aspects, the extract further comprises from 17 to 46% w/w 1,3-dihydroxyacetone. In some aspects, the extract further comprises from 18 to 46% w/w 1,3-dihydroxyacetone. In some aspects, the extract further comprises from 19 to 46% w/w 1,3-dihydroxyacetone. In some aspects, the extract further comprises from 20 to 46% w/w 1,3-dihydroxyacetone. In some aspects, the extract further comprises from 21 to 46% w/w 1,3-dihydroxyacetone. In some aspects, the extract further comprises from 22 to 46% w/w 1,3-dihydroxyacetone. In some aspects, the extract further comprises from 23 to 46% w/w 1,3-dihydroxyacetone. In some aspects, the extract further comprises from 24 to 46% w/w 1,3-dihydroxyacetone. In some aspects, the extract further comprises from 25 to 46% w/w 1,3-dihydroxyacetone. In some aspects, the extract further comprises from 26 to 46% w/w 1,3-dihydroxyacetone. In some aspects, the extract further comprises from 27 to 46% w/w 1,3-dihydroxyacetone. In some aspects, the extract further comprises from 28 to 46% w/w 1,3-dihydroxyacetone. In some aspects, the extract further comprises from 29 to 46% w/w 1,3-dihydroxyacetone. In some aspects, the extract further comprises from 30 to 46% w/w 1,3-dihydroxyacetone. In some aspects, the extract further comprises from 31 to 46% w/w 1,3-dihydroxyacetone. In some aspects, the extract further comprises from 32 to 46% w/w 1,3-dihydroxyacetone. In some aspects, the extract further comprises from 33 to 46% w/w 1,3-dihydroxyacetone. In some aspects, the extract further comprises from 34 to 46% w/w 1,3-dihydroxyacetone. In some aspects, the extract further comprises from 35 to 46% w/w 1,3-dihydroxyacetone. In some aspects, the extract further comprises from 36 to 46% w/w 1,3-dihydroxyacetone. In some aspects, the extract further comprises from 37 to 46% w/w 1,3-dihydroxyacetone. In some aspects, the extract further comprises from 38 to 46% w/w 1,3-dihydroxyacetone. In some aspects, the extract further comprises from 39 to 46% w/w 1,3-dihydroxyacetone. In some aspects, the extract further comprises from 40 to 46% w/w 1,3-dihydroxyacetone. In some aspects, the extract further comprises from 41 to 46% w/w 1,3-dihydroxyacetone. In some aspects, the extract further comprises from 42 to 46% w/w 1,3-dihydroxyacetone. In some aspects, the extract further comprises from 43 to 46% w/w 1,3-dihydroxyacetone. In some aspects, the extract further comprises from 44 to 46% w/w 1,3-dihydroxyacetone. In some aspects, the extract further comprises from 45 to 46% w/w 1,3-dihydroxyacetone.

In some aspects, the extract further comprises from 6 to 45% w/w 1,3-dihydroxyacetone. In some aspects, the extract further comprises from 6 to 44% w/w 1,3-dihydroxyacetone. In some aspects, the extract further comprises from 6 to 45% w/w 1,3-dihydroxyacetone. In some aspects, the extract further comprises from 6 to 42% w/w 1,3-dihydroxyacetone. In some aspects, the extract further comprises from 6 to 41% w/w 1,3-dihydroxyacetone. In some aspects, the extract further comprises from 6 to 40% w/w 1,3-dihydroxyacetone. In some aspects, the extract further comprises from 6 to 39% w/w 1,3-dihydroxyacetone. In some aspects, the extract further comprises from 6 to 38% w/w 1,3-dihydroxyacetone. In some aspects, the extract further comprises from 6 to 37% w/w 1,3-dihydroxyacetone. In some aspects, the extract further comprises from 6 to 36% w/w 1,3-dihydroxyacetone. In some aspects, the extract further comprises from 6 to 35% w/w 1,3-dihydroxyacetone. In some aspects, the extract further comprises from 6 to 34% w/w 1,3-dihydroxyacetone. In some aspects, the extract further comprises from 6 to 33% w/w 1,3-dihydroxyacetone. In some aspects, the extract further comprises from 6 to 32% w/w 1,3-dihydroxyacetone. In some aspects, the extract further comprises from 6 to 31% w/w 1,3-dihydroxyacetone. In some aspects, the extract further comprises from 6 to 30% w/w 1,3-dihydroxyacetone. In some aspects, the extract further comprises from 6 to 29% w/w 1,3-dihydroxyacetone. In some aspects, the extract further comprises from 6 to 28% w/w 1,3-dihydroxyacetone. In some aspects, the extract further comprises from 6 to 27% w/w 1,3-dihydroxyacetone. In some aspects, the extract further comprises from 6 to 26% w/w 1,3-dihydroxyacetone. In some aspects, the extract further comprises from 6 to 25% w/w 1,3-dihydroxyacetone. In some aspects, the extract further comprises from 6 to 24% w/w 1,3-dihydroxyacetone. In some aspects, the extract further comprises from 6 to 23% w/w 1,3-dihydroxyacetone. In some aspects, the extract further comprises from 6 to 22% w/w 1,3-dihydroxyacetone. In some aspects, the extract further comprises from 6 to 21% w/w 1,3-dihydroxyacetone. In some aspects, the extract further comprises from 6 to 20% w/w 1,3-dihydroxyacetone. In some aspects, the extract further comprises from 6 to 19% w/w 1,3-dihydroxyacetone. In some aspects, the extract further comprises from 6 to 18% w/w 1,3-dihydroxyacetone. In some aspects, the extract further comprises from 6 to 17% w/w 1,3-dihydroxyacetone. In some aspects, the extract further comprises from 6 to 16% w/w 1,3-dihydroxyacetone. In some aspects, the extract further comprises from 6 to 15% w/w 1,3-dihydroxyacetone. In some aspects, the extract further comprises from 6 to 14% w/w 1,3-dihydroxyacetone. In some aspects, the extract further comprises from 6 to 13% w/w 1,3-dihydroxyacetone. In some aspects, the extract further comprises from 6 to 12% w/w 1,3-dihydroxyacetone. In some aspects, the extract further comprises from 6 to 11% w/w 1,3-dihydroxyacetone. In some aspects, the extract further comprises from 6 to 10% w/w 1,3-dihydroxyacetone. In some aspects, the extract further comprises from 6 to 9% w/w 1,3-dihydroxyacetone. In some aspects, the extract further comprises from 6 to 8% w/w 1,3-dihydroxyacetone. In some aspects, the extract further comprises from 6 to 7% w/w 1,3-dihydroxyacetone.

In some aspects, the extract further comprises 6, or 7, or 8, or 9, or 10, or 11, or 12, or 13, or 14, or 15, or 16, or 17, or 18, or 19, or 20, or 21, or 22, or 23, or 24, or 25, or 26, or 27, or 28, or 29, or 30, or 31, or 32, or 33, or 34, or 35, or 36, or 37, or 38, or 39, or 40, or 41, or 42, or 43, or 44, or 45, or 46% w/w 1,3-dihydroxyacetone.

In some aspects, the extract further comprises from 0.2 to 7% w/w 1,3-octanediol. In some aspects, the extract further comprises from 0.4 to 7% w/w 1,3-octanediol. In some aspects, the extract further comprises from 0.6 to 7% w/w 1,3-octanediol. In some aspects, the extract further comprises from 0.8 to 7% w/w 1,3-octanediol. In some aspects, the extract further comprises from 1 to 7% w/w 1,3-octanediol. In some aspects, the extract further comprises from 1.2 to 7% w/w 1,3-octanediol. In some aspects, the extract further comprises from 1.4 to 7% w/w 1,3-octanediol. In some aspects, the extract further comprises from 1.6 to 7% w/w 1,3-octanediol. In some aspects, the extract further comprises from 1.8 to 7% w/w 1,3-octanediol. In some aspects, the extract further comprises from 2 to 7% w/w 1,3-octanediol. In some aspects, the extract further comprises from 2.2 to 7% w/w 1,3-octanediol.

In some aspects, the extract further comprises from 2.4 to 7% w/w 1,3-octanediol. In some aspects, the extract further comprises from 2.6 to 7% w/w 1,3-octanediol. In some aspects, the extract further comprises from 2.8 to 7% w/w 1,3-octanediol. In some aspects, the extract further comprises from 3 to 7% w/w 1,3-octanediol. In some aspects, the extract further comprises from 3.2 to 7% w/w 1,3-octanediol. In some aspects, the extract further comprises from 3.4 to 7% w/w 1,3-octanediol. In some aspects, the extract further comprises from 3.6 to 7% w/w 1,3-octanediol. In some aspects, the extract further comprises from 3.8 to 7% w/w 1,3-octanediol. In some aspects, the extract further comprises from 4 to 7% w/w 1,3-octanediol. In some aspects, the extract further comprises from 4.2 to 7% w/w 1,3-octanediol. In some aspects, the extract further comprises from 4.4 to 7% w/w 1,3-octanediol. In some aspects, the extract further comprises from 4.6 to 7% w/w 1,3-octanediol. In some aspects, the extract further comprises from 4.8 to 7% w/w 1,3-octanediol. In some aspects, the extract further comprises from 5 to 7% w/w 1,3-octanediol. In some aspects, the extract further comprises from 5.2 to 7% w/w 1,3-octanediol. In some aspects, the extract further comprises from 5.4 to 7% w/w 1,3-octanediol. In some aspects, the extract further comprises from 5.6 to 7% w/w 1,3-octanediol. In some aspects, the extract further comprises from 5.8 to 7% w/w 1,3-octanediol. In some aspects, the extract further comprises from 6 to 7% w/w 1,3-octanediol. In some aspects, the extract further comprises from 6.2 to 7% w/w 1,3-octanediol. In some aspects, the extract further comprises from 6.4 to 7% w/w 1,3-octanediol. In some aspects, the extract further comprises from 6.6 to 7% w/w 1,3-octanediol. In some aspects, the extract further comprises from 6.8 to 7% w/w 1,3-octanediol.

In some aspects, the extract further comprises from 0.2 to 6.8% w/w 1,3-octanediol. In some aspects, the extract further comprises from 0.2 to 6.4% w/w 1,3-octanediol. In some aspects, the extract further comprises from 0.2 to 6.2% w/w 1,3-octanediol. In some aspects, the extract further comprises from 0.2 to 6% w/w 1,3-octanediol. In some aspects, the extract further comprises from 0.2 to 5.8% w/w 1,3-octanediol. In some aspects, the extract further comprises from 0.2 to 5.4% w/w 1,3-octanediol. In some aspects, the extract further comprises from 0.2 to 5.2% w/w 1,3-octanediol. In some aspects, the extract further comprises from 0.2 to 5% w/w 1,3-octanediol. In some aspects, the extract further comprises from 0.2 to 4.8% w/w 1,3-octanediol. In some aspects, the extract further comprises from 0.2 to 4.4% w/w 1,3-octanediol. In some aspects, the extract further comprises from 0.2 to 4.2% w/w 1,3-octanediol. In some aspects, the extract further comprises from 0.2 to 4% w/w 1,3-octanediol. In some aspects, the extract further comprises from 0.2 to 3.8% w/w 1,3-octanediol. In some aspects, the extract further comprises from 0.2 to 3.4% w/w 1,3-octanediol. In some aspects, the extract further comprises from 0.2 to 3.2% w/w 1,3-octanediol. In some aspects, the extract further comprises from 0.2 to 3% w/w 1,3-octanediol. In some aspects, the extract further comprises from 0.2 to 2.8% w/w 1,3-octanediol. In some aspects, the extract further comprises from 0.2 to 2.4% w/w 1,3-octanediol. In some aspects, the extract further comprises from 0.2 to 2.2% w/w 1,3-octanediol. In some aspects, the extract further comprises from 0.2 to 2% w/w 1,3-octanediol. In some aspects, the extract further comprises from 0.2 to 1.8% w/w 1,3-octanediol. In some aspects, the extract further comprises from 0.2 to 1.4% w/w 1,3-octanediol. In some aspects, the extract further comprises from 0.2 to 1.2% w/w 1,3-octanediol. In some aspects, the extract further comprises from 0.2 to 1% w/w 1,3-octanediol. In some aspects, the extract further comprises from 0.2 to 0.8% w/w 1,3-octanediol. In some aspects, the extract further comprises from 0.2 to 0.4% w/w 1,3-octanediol.

In some aspects, the extract further comprises 0.2, or 0.4, or 0.6, or 0.8, or 1, or 1.2, or 1.4, or 1.6, or 1.8, or 2, or 2.2, or 2.4, or 2.6, or 2.8, or 3, or 3.2, or 3.4, or 3.6, or 3.8, or 4, or 4.2, or 4.4, or 4.6, or 4.8, or 5, or 5.2, or 5.4, or 5.6, or 5.8, or 6, or 6.2, or 6.4, or 6.6, or 6.8, or 7% w/w 1,3-octanediol.

In some aspects, the extract further comprises from 0.5 to 4% w/w 5-hydroxy-5,6-dihydrolmaltol. In some aspects, the extract further comprises from 1 to 4% w/w 5-hydroxy-5,6-dihydrolmaltol. In some aspects, the extract further comprises from 1.5 to 4% w/w 5-hydroxy-5,6-dihydrolmaltol. In some aspects, the extract further comprises from 2 to 4% w/w 5-hydroxy-5,6-dihydrolmaltol. In some aspects, the extract further comprises from 2.5 to 4% w/w 5-hydroxy-5,6-dihydrolmaltol. In some aspects, the extract further comprises from 3 to 4% w/w 5-hydroxy-5,6-dihydrolmaltol. In some aspects, the extract further comprises from 3.5 to 4% w/w 5-hydroxy-5,6-dihydrolmaltol.

In some aspects, the extract further comprises from 0.5 to 3.5% w/w 5-hydroxy-5,6-dihydrolmaltol. In some aspects, the extract further comprises from 0.5 to 3% w/w 5-hydroxy-5,6-dihydrolmaltol. In some aspects, the extract further comprises from 0.5 to 2.5% w/w 5-hydroxy-5,6-dihydrolmaltol. In some aspects, the extract further comprises from 0.5 to 2% w/w 5-hydroxy-5,6-dihydrolmaltol. In some aspects, the extract further comprises from 0.5 to 1.5% w/w 5-hydroxy-5,6-dihydrolmaltol. In some aspects, the extract further comprises from 0.5 to 1% w/w 5-hydroxy-5,6-dihydrolmaltol.

In some aspects, the extract further comprises 0.5, or 1, or 1.5, or 2, or 2.5, or 3, or 3.5, or 4% w/w 5-hydroxy-5,6-dihydrolmaltol.

In some aspects, the extract further comprises from 1 to 4% w/w 5-hydroxymethyl furfural. In some aspects, the extract further comprises from 2 to 4% w/w 5-hydroxymethyl furfural. In some aspects, the extract further comprises from 3 to 4% w/w 5-hydroxymethyl furfural.

In some aspects, the extract further comprises from 1 to 3% w/w 5-hydroxymethyl furfural. In some aspects, the extract further comprises from 1 to 2% w/w 5-hydroxymethyl furfural.

In some aspects, the extract further comprises 1, or 2, or 3, or 4% w/w 5-hydroxymethyl furfural.

In some aspects, the extract comprises the compounds, at the amounts disclosed in any one of Microwave Extract 1, or Microwave Extract 2 disclosed in Table 3.

Extract Derived from Green Tea Leaves: One aspect presented herein provides an extract from green tea leaves, wherein the extract comprises at least 12% w/w caffeine.

In some aspects, the extract comprises from 12 to 30% w/w caffeine.

In some aspects, the extract further comprises less than 8% furfuryl alcohol.

In some aspects, the extract further comprises 3,5-octadien-2-one, β-ionone, and 4,5-epoxy-β-ionone.

In some aspects, the extract comprises the compounds, at the amounts disclosed in any one of Microwave Extract 1, or Microwave Extract 2 disclosed in Table 4.

Extract Derived from Roasted Coffee Beans: One aspect presented herein provides an extract from roasted coffee beans, wherein the extract comprises at least 2% w/w coffee furanone.

In some aspects, the extract comprises from 2 to 2.5% w/w coffee furanone. In some aspects, the extract comprises from 2.1 to 2.5% w/w coffee furanone. In some aspects, the extract comprises from 2.2 to 2.5% w/w coffee furanone. In some aspects, the extract comprises from 2.3 to 2.5% w/w coffee furanone. In some aspects, the extract comprises from 2.4 to 2.5% w/w coffee furanone.

In some aspects, the extract comprises from 2 to 2.4% w/w coffee furanone. In some aspects, the extract comprises from 2 to 2.3% w/w coffee furanone. In some aspects, the extract comprises from 2 to 2.2% w/w coffee furanone. In some aspects, the extract comprises from 2 to 2.1% w/w coffee furanone.

In some aspects, the extract comprises 2, or 2.1, or 2.2, or 2.3, or 2.4, or 2.5% w/w coffee furanone.

In some aspects, the extract further comprises from 3 to 4% w/w 2-methyl pyrazine. In some aspects, the extract further comprises from 3.1 to 4% w/w 2-methyl pyrazine. In some aspects, the extract further comprises from 3.2 to 4% w/w 2-methyl pyrazine. In some aspects, the extract further comprises from 3.3 to 4% w/w 2-methyl pyrazine. In some aspects, the extract further comprises from 3.4 to 4% w/w 2-methyl pyrazine. In some aspects, the extract further comprises from 3.5 to 4% w/w 2-methyl pyrazine. In some aspects, the extract further comprises from 3.6 to 4% w/w 2-methyl pyrazine. In some aspects, the extract further comprises from 3.7 to 4% w/w 2-methyl pyrazine. In some aspects, the extract further comprises from 3.8 to 4% w/w 2-methyl pyrazine. In some aspects, the extract further comprises from 3.9 to 4% w/w 2-methyl pyrazine.

In some aspects, the extract further comprises from 3 to 3.9% w/w 2-methyl pyrazine. In some aspects, the extract further comprises from 3 to 3.8% w/w 2-methyl pyrazine. In some aspects, the extract further comprises from 3 to 3.7% w/w 2-methyl pyrazine. In some aspects, the extract further comprises from 3 to 3.6% w/w 2-methyl pyrazine. In some aspects, the extract further comprises from 3 to 3.5% w/w 2-methyl pyrazine. In some aspects, the extract further comprises from 3 to 3.4% w/w 2-methyl pyrazine. In some aspects, the extract further comprises from 3 to 3.3% w/w 2-methyl pyrazine. In some aspects, the extract further comprises from 3 to 3.2% w/w 2-methyl pyrazine. In some aspects, the extract further comprises from 3 to 3.1% w/w 2-methyl pyrazine.

In some aspects, the extract further comprises 3, or 3.1, or 3.2, or 3.3, or 3.4, or 3.5, or 3.6, or 3.7, or 3.8, or 3.9, or 4% w/w 2-methyl pyrazine.

In some aspects, the extract further comprises from 0.5 to 2% w/w acetylmethyl carbinol. In some aspects, the extract further comprises from 1 to 2% w/w acetylmethyl carbinol. In some aspects, the extract further comprises from 1.5 to 2% w/w acetylmethyl carbinol.

In some aspects, the extract further comprises from 0.5 to 1.5% w/w acetylmethyl carbinol. In some aspects, the extract further comprises from 0.5 to 1% w/w acetylmethyl carbinol.

In some aspects, the extract further comprises 0.5, or 1, or 1.5, or 2% w/w acetylmethyl carbinol.

In some aspects, the extract further comprises from 0.5 to 8% w/w acetol. In some aspects, the extract further comprises from 1 to 8% w/w acetol. In some aspects, the extract further comprises from 1.5 to 8% w/w acetol. In some aspects, the extract further comprises from 2 to 8% w/w acetol. In some aspects, the extract further comprises from 2.5 to 8% w/w acetol. In some aspects, the extract further comprises from 3 to 8% w/w acetol. In some aspects, the extract further comprises from 3.5 to 8% w/w acetol. In some aspects, the extract further comprises from 4 to 8% w/w acetol. In some aspects, the extract further comprises from 4.5 to 8% w/w acetol. In some aspects, the extract further comprises from 5 to 8% w/w acetol. In some aspects, the extract further comprises from 5.5 to 8% w/w acetol. In some aspects, the extract further comprises from 6 to 8% w/w acetol. In some aspects, the extract further comprises from 6.5 to 8% w/w acetol. In some aspects, the extract further comprises from 7 to 8% w/w acetol. In some aspects, the extract further comprises from 7.5 to 8% w/w acetol.

In some aspects, the extract further comprises from 0.5 to 7.5% w/w acetol. In some aspects, the extract further comprises from 0.5 to 7% w/w acetol. In some aspects, the extract further comprises from 0.5 to 6.5% w/w acetol. In some aspects, the extract further comprises from 0.5 to 6% w/w acetol. In some aspects, the extract further comprises from 0.5 to 5.5% w/w acetol. In some aspects, the extract further comprises from 0.5 to 5% w/w acetol. In some aspects, the extract further comprises from 0.5 to 4.5% w/w acetol. In some aspects, the extract further comprises from 0.5 to 4% w/w acetol. In some aspects, the extract further comprises from 0.5 to 3.5% w/w acetol. In some aspects, the extract further comprises from 0.5 to 5% w/w acetol. In some aspects, the extract further comprises from 0.5 to 2.5% w/w acetol. In some aspects, the extract further comprises from 0.5 to 2% w/w acetol. In some aspects, the extract further comprises from 0.5 to 1.5% w/w acetol. In some aspects, the extract further comprises from 0.5 to 1% w/w acetol.

In some aspects, the extract further comprises 0.5, or 1, or 1.5, or 2, or 2.5, or 3, or 3.5, or 4, or 4.5, or 5, or 5.5, or 6, or 6.5, or 7, or 7.5, or 8% w/w acetol.

In some aspects, the extract further comprises from 35 to 45% w/w furfuryl alcohol. In some aspects, the extract further comprises from 36 to 45% w/w furfuryl alcohol. In some aspects, the extract further comprises from 37 to 45% w/w furfuryl alcohol. In some aspects, the extract further comprises from 38 to 45% w/w furfuryl alcohol. In some aspects, the extract further comprises from 39 to 45% w/w furfuryl alcohol. In some aspects, the extract further comprises from 40 to 45% w/w furfuryl alcohol. In some aspects, the extract further comprises from 41 to 45% w/w furfuryl alcohol. In some aspects, the extract further comprises from 42 to 45% w/w furfuryl alcohol. In some aspects, the extract further comprises from 43 to 45% w/w furfuryl alcohol. In some aspects, the extract further comprises from 44 to 45% w/w furfuryl alcohol.

In some aspects, the extract further comprises from 35 to 44% w/w furfuryl alcohol. In some aspects, the extract further comprises from 35 to 43% w/w furfuryl alcohol. In some aspects, the extract further comprises from 35 to 42% w/w furfuryl alcohol. In some aspects, the extract further comprises from 35 to 41% w/w furfuryl alcohol. In some aspects, the extract further comprises from 35 to 40% w/w furfuryl alcohol. In some aspects, the extract further comprises from 35 to 39% w/w furfuryl alcohol. In some aspects, the extract further comprises from 35 to 38% w/w furfuryl alcohol. In some aspects, the extract further comprises from 35 to 37% w/w furfuryl alcohol. In some aspects, the extract further comprises from 35 to 36% w/w furfuryl alcohol.

In some aspects, the extract further comprises 35, or 36, or 37, or 38, or 39, or 40, or 41, or 42, or 43, or 44, or 45% w/w furfuryl alcohol.

In some aspects, the extract further comprises 0.2% w/w 2-cyclopentenone.

In some aspects, the extract comprises the compounds, at the amounts disclosed in any one of Microwave Extract 1, or Microwave Extract 2 disclosed in Table 6.

Without intending to be limited to any particular theory, the differences in the coffee extract obtained according to a method according to the aspects presented herein differs from a commercially obtained extract in volatile compounds that contribute to the sweet notes and olfactive profile of fresh coffee.

Compositions Comprising an Extract According to Some Aspects Presented Herein

It is understood by a person skilled in the art that an extract according to some aspects presented herein may be added into a composition described herein in neat form, or in a solvent. Alternatively, an extract according to some aspects presented herein may first be modified, for example by entrapped with an entrapment material such as for example polymers, capsules, microcapsules, nanocapsules, liposomes, precursors, film formers, absorbents such as for example by using carbon or zeolites, cyclic oligosaccharides and mixtures thereof.

Accordingly, some aspects presented herein provide a composition comprising:
  a. an extract according to some aspects presented herein;
  b. at least one ingredient selected from the group consisting of a perfumery carrier and a perfumery base; and
  c. optionally at least one perfumery adjuvant.

As used herein, the term "perfumery carrier" refers to a material which is practically neutral from a perfumery point of view, i.e. which does not significantly alter the organoleptic properties of perfuming ingredients. The perfumery carrier may be a liquid or a solid.

Non-limiting examples of liquid perfumery carriers include an emulsifying system, i.e. a solvent and a surfactant system, or a solvent commonly used in perfumery. A detailed description of the nature and type of solvents commonly used in perfumery cannot be exhaustive. However, non-limiting examples solvents include dipropyleneglycol, diethyl phthalate, isopropyl myristate, benzyl benzoate, 2-(2-ethoxyethoxy)-1-ethanol or ethyl citrate. For the compositions which comprise both a perfumery carrier and a perfumery base, other suitable perfumery carriers than those previously specified, can be also ethanol, water/ethanol mixtures, limonene or other terpenes, isoparaffins such as those known under the trademark Isopar® (origin: Exxon Chemical) or glycol ethers and glycol ether esters such as those known under the trademark Dowanol® (origin: Dow Chemical Company).

Non-limiting examples of solid perfumery carriers include absorbing gums or polymers, or yet encapsulating materials. Examples of such materials may comprise wall-forming and plasticizing materials, such as mono, di- or trisaccharides, natural or modified starches, hydrocolloids, cellulose derivatives, polyvinyl acetates, polyvinylalcohols, proteins or pectins, or yet the materials cited in reference texts such as H. Scherz, Hydrokolloide: Stabilisatoren, Dickungs- and Geliermittel in Lebensmitteln, Band 2 der Schriftenreihe Lebensmittelchemie, Lebensmittelqualität, Behr's Verlag GmbH & Co., Hamburg, 1996. The encapsulation is a well-known process to a person skilled in the art, and may be performed, for instance, using techniques such as spray-drying, agglomeration or yet extrusion; or consists of a coating encapsulation, including coacervation and complex coacervation technique.

As used herein, the term "perfumery base" refers a composition comprising at least one perfuming co-ingredient. A perfuming co-ingredient does not include a compound of formula (I). As used herein, the term "perfuming co-ingredient" refers to compound, which is used in a perfuming preparation or a composition to impart a hedonic effect. In other words such a co-ingredient, to be considered as being a perfuming one, must be recognized by a person skilled in the art as being able to impart or modify in a positive or pleasant way the odor of a composition, and not just as having an odor.

The nature and type of the perfuming co-ingredients present in the base do not warrant a more detailed description here, which in any case would not be exhaustive, the skilled person being able to select them on the basis of his general knowledge and according to intended use or application and the desired organoleptic effect. In general terms, these perfuming co-ingredients belong to chemical classes as varied as alcohols, lactones, aldehydes, ketones, esters, ethers, acetates, nitriles, terpenoids, nitrogenous or sulphurous heterocyclic compounds and essential oils, and said perfuming co-ingredients can be of natural or synthetic origin. Many of these co-ingredients are in any case listed in reference texts such as the book by S. Arctander, Perfume and Flavor Chemicals, 1969, Montclair, New Jersey, USA, or its more recent versions, or in other works of a similar nature, as well as in the abundant patent literature in the field of perfumery. It is also understood that said co-ingredients may also be compounds known to release in a controlled manner various types of perfuming compounds.

As used herein, the term "perfumery adjuvant" refers to an ingredient capable of imparting additional added benefit such as a color, a particular light resistance, chemical stability, etc. A detailed description of the nature and type of adjuvant commonly used in perfuming bases cannot be exhaustive, but it has to be mentioned that said ingredients are well known to a person skilled in the art.

Accordingly, in some aspects, the present disclosure provides a perfumed consumer product comprising an effective amount of an extract according to some aspects presented herein. In some aspects, the perfumed consumer product is selected from the group consisting of: air care products, home care products and laundry care products.

In some aspects, the perfumed consumer product comprising an effective amount of an extract according to some aspects presented herein comprises a formulation selected from the group consisting of: aerosol and/or water-based air freshener spray, wick/reed air freshener, liquid electrical (plug-in) air freshener, a solid support air freshener, gel-based air freshener, membrane-containing air freshener, bleaching, cleaning, washing detergent powder, liquid all-purpose cleaner, specialty cleaner and liquid detergent.

It should be appreciated by those skilled in the art that the conception and the specific embodiments disclosed might be readily utilized as a basis for modifying or formulating other formulations for carrying the same purposes of the present invention. It should also be realized by those skilled in the art that such equivalent formulations do not depart from the spirit and scope of the disclosure as set forth in the appended claims.

The proportions in which an extract according to some aspects presented herein can be incorporated into the various aforementioned products or compositions vary within a wide range of values. These values are dependent on the nature of the consumer product and on the desired organoleptic effect as well as the nature of the co-ingredients in a given composition when the extract according to some aspects presented herein are mixed with other ingredients, solvents or additives commonly used in the art.

In general, for example, in the case of perfuming compositions, typical concentrations are in the order of 0.001% to 5% by weight, or even more, of an extract according to some aspects presented herein, based on the weight of the composition into which they are incorporated. Concentrations lower than these, such as in the order of 0.01% to 100% by weight, can be used when the compositions described herein are incorporated into consumer products, the percentage being relative to the weight of the consumer product.

In particular, the concentration of a composition according to the aspects described herein, used in the various aforementioned consumer products varies within a various wide range of values depending on the nature of the consumer product. For instance, a composition according some aspects described herein can be used in a perfume product at a concentration of 0.01% to 50% by weight, alternatively at a concentration of 0.2% to 40% by weight, alternatively at a concentration of 0.5% to 25% by weight. For instance, a composition according to some aspects described herein can be used in a fabric care product at a concentration of 0.01% to 20% by weight, alternatively at a concentration of 0.05% to 10% by weight, alternatively at a concentration of 0.1% to 5% by weight. For instance, a composition according to some aspects described herein can be used in a hair care product at a concentration of 0.01% to 10% by weight, alternatively at a concentration of 0.05% to 5% by weight, alternatively at a concentration of 0.1% to 3% by weight. For instance, a composition according to some aspects described herein can be used in a skin care product at a concentration of 0.01% to 10% by weight, alternatively at a concentration of 0.05% to 5% by weight, most preferably at a concentration of 0.1% to 2.5% by weight. For instance, a composition according to some aspects described herein can be used in a body deodorant or antiperspirant product at a concentration of 0.01% to 10% by weight, alternatively at a concentration of 0.05% to 7% by weight, alternatively at a concentration of 0.1% to 5% by weight. For instance, a composition according to some aspects described herein can be used in a skin cleansing product at a concentration of 0.01% to 5% by weight, alternatively at a concentration of 0.05% to 3% by weight, alternatively at a concentration of 0.1% to 2.5% by weight. For instance, a composition according to some aspects described herein can be used in an air freshening product at a concentration of 0.01% to 100% by weight. For instance, a composition according to some aspects described herein can be used in a surface care product at a concentration of 0.001% to 10% by weight, alternatively at a concentration of 0.01% to 5% by weight, alternatively at a concentration of 0.1% to 2% by weight. Yet, for instance, a composition according to some aspects described herein can be used in a pet-litter product at a concentration of 0.001% to 1% by weight, alternatively at a concentration of 0.005% to 0.5% by weight, alternatively at a concentration of 0.01% to 0.3% by weight.

In some aspects, the composition as defined in any of the above aspect may be absorbed on a porous or non-porous substrate in loose powder or compacted form, the substrate being selected from cellulose (paper/cardboard), vermiculite, other industrial absorbents, perlite, calcium carbonate, pumice, wood, sawdust, ground corn cob, ground rice hull, rice hull ash, biochars, starches, modified starches and mixtures thereof.

One aspect presented herein provides a perfumed article containing the essential oil according to some aspects presented herein, wherein the perfumed article is selected from the group consisting of: an aromatic water, a perfume, a cologne, a bath gel, a shower gel, a shampoo, a hair care product, a cosmetic preparation, a deodorant, an air freshener, a detergent, a fabric softener, and a household cleaner.

Non-limiting examples of suitable consumer product include:
  a perfume, such as a fine perfume, an Eau de Toilette, a cologne or an after-shave lotion;
  a fabric care product, such as a liquid detergent, a powder detergent, detergent tablets, a detergent bar, a detergent paste, a liquid fabric softener, fabric softener sheets, a fabric scent booster, a laundry pre-treatment, a fabric refresher, an ironing water, a laundry bleach, a carpet powder or a carpet cleaner;
  a hair care product, such as a shampoo, a hair conditioner, a hair cream, a hair oil, a hair styling product (such as a spray, mousse or gel), a hair coloration product or a hair permanent wave product;
  a skin care product, such as a face cream, a face lotion, a shaving product (such as a foam, cream, gel or oil), a body and/or hand product (such as a lotion, cream, gel or oil), a skin firming product, a depilatory, a talcum powder, a foot care cream or lotion, baby wipes, cleansing wipes, moisturizer wipes, a sun-protection product (such as a spray, lotion, cream or oil), an after-sun lotion, or a self-tanning product;
  a body deodorant or antiperspirant product, such as a body deodorant spray, a roll-on deodorant, a deodorant stick, a deodorant cream, an antiperspirant spray, an antiperspirant stick, a roll-on antiperspirant liquid, an antiperspirant stick, or an antiperspirant cream;
  a skin-cleansing product, such as a soap bar, a shower gel, a liquid hand soap, a bath foam or an intimate wash product;
  an air freshening product, such as an air freshener spray, a gel air freshener, a liquid-wick air freshener, a solid air freshener comprising a porous substrate (such as a paper or card blotter, a porous ceramic, or a porous plastic), a liquid or gel air freshener comprising a permeable membrane, an electrically operated air freshener, and a dual purpose air freshener/disinfectant spray; and/or a surface care product, such as an all-purpose cleaner, a furniture polish, a wood floor cleaner, a window cleaner, a hand dishwashing product (such as a liquid, gel or paste), a machine dishwashing product (such as a powder, liquid, gel, tablet or sachet), a toilet bowl cleaning liquid, an in-cistern toilet cleaner, a toilet rim block, or a toilet rim liquid; a pet-litter.

The present invention is best illustrated but is not limited to the following examples, wherein the abbreviations have the usual meaning in the art.

EXAMPLES

Example 1

Extracting Essential Oils from *Jasminium Grandiflorum*

Referring to FIG. 3, freshly isolated flowers from *Jasminium grandiflorum* were introduced into a microwave extractor at a rate of 4 Kg per hour. The length of the microwave extractor was 2.5 m. The freshly isolated flowers were subjected to microwave energy at a power of 200 Watts (a power of 0.56 KWH per Kg biomass), to obtain a distillate, while the temperature of the chamber within the microwave extractor (referring to FIGS. 1 and 2 for example), was maintained at a temperature between 60 and 80 degrees Celsius. The transit time of the plant biomass through the microwave extractor was approximately 20 minutes.

The distillate was collected at the bottom of the microwave extractor by gravimetry, and the distillate was applied to a XAD4 resin column. Once the resin in the column became saturated, materials bound to the resin column were desorbed, using ethanol, with a flow rate of approximately 5 bed volumes per hour, wherein the total volume was adjusted to result in a composition comprising essential oils having the desired concentration in ethanol. Here, approximately 3 to 15 bed volumes were required to elute the essential oil off the resin column.

In some experiments, the distillate collected from the microwave extractor, prior to application to the XAD4 resin column comprised essential oils having a concentration from 200 to 3000 ppm. The composition of the essential oils was analyzed by GC, and the results are reported in Table 1 of Example 2 below.

Example 2

Essential Oils from *Jasminium Grandiflorum*

The results of the CG analysis of three compositions comprising distillate collected from the microwave extractor, prior to application to the XAD4 resin column from three separate experiments are reported in Table 1 below. For comparison, the constituents of essential oils from four commercial sources are included. The sensory properties of the essential oils were also evaluated.

TABLE 1

| Compound | Microwave Extract 1% w/w GC | Microwave Extract 2% w/w GC | Microwave Extract 3% w/w GC | Commercial Jasmin Extract 1% w/w GC | Commercial Jasmin Extract 1% w/w GC | Commercial Jasmin Extract 3% w/w GC | Commercial Jasmin Extract 4% w/w GC |
|---|---|---|---|---|---|---|---|
| BENZYL ALCOHOL | 0.20 | 0.63 | 0.67 | 3.25 | 1.76 | 1.47 | 1.55 |
| PHENYLACETALDEHYDE | tr | tr | 0.30 | tr | tr | tr | tr |
| p-CRESOL | 0.10 | 0.13 | 0.25 | 0.21 | 0.15 | 0.42 | 2.19 |
| METHYL BENZOATE | nd | nd | tr | 0.14 | nd | tr | 0.25 |
| LINALOOL | 12.98 | 11.77 | 16.92 | 4.02 | 1.76 | 3.84 | 3.59 |
| BENZYL CYANIDE | 0.11 | tr | tr | tr | nd | nd | nd |
| BENZYL ACETATE | 41.89 | 37.17 | 61.58 | 11.63 | 5.87 | 11.36 | 16.08 |
| a-TERPINEOL | tr | tr | 1.40 | tr | tr | tr | tr |
| NEROL | tr | tr | 0.19 | tr | tr | tr | tr |
| GERANIOL | tr | tr | 0.65 | tr | tr | tr | tr |
| INDOLE | 6.48 | 2.78 | 1.17 | tr | tr | 0.55 | 3.40 |
| METHYL ANTHRANILATE | 0.93 | 0.74 | 0.46 | nd | nd | nd | nd |
| EUGENOL | 0.45 | 0.51 | 0.61 | 1.03 | 0.32 | 1.48 | 1.60 |
| (Z)-JASMONE | 10.23 | 5.45 | 7.69 | 1.61 | 2.91 | 1.54 | 6.45 |
| JASMIN LACTONE | 1.12 | 0.64 | tr | 0.48 | 0.83 | 0.69 | 1.76 |
| (E,E)-FARNESENE | 5.28 | 6.02 | 1.29 | 1.87 | 1.81 | 0.79 | 2.26 |
| (Z)-3-HEXENYL BENZOATE | 2.01 | 3.22 | 0.68 | 0.85 | 1.20 | 0.77 | 1.25 |
| (E)-NEROLIDOL | 0.17 | 0.24 | tr | tr | 0.21 | 0.11 | 0.35 |
| METHYL N-ACETYL ANTHRANILATE | 0.21 | 0.14 | tr | 0.34 | 0.80 | tr | tr |
| (E,E)-4,8,12-TRIMETHYL-1,3,7,11-TRIDECATETRAENE | 0.21 | 0.21 | tr | tr | tr | tr | tr |
| METHYL (Z)-JASMONATE | 0.24 | 0.19 | tr | 0.80 | 0.67 | 0.35 | 1.01 |
| METHYL (E)-EPIJASMONATE | 0.39 | 0.28 | tr | tr | 0.53 | tr | tr |
| JASMIN KETOLACTONE | 0.11 | tr | nd | 0.31 | 0.64 | 0.27 | tr |
| BENZYL BENZOATE | 3.26 | 7.16 | 1.40 | 6.45 | 6.76 | 12.45 | 12.44 |
| HEXAHYDROFARNESYL ACETONE | 0.84 | 1.78 | 0.32 | 1.54 | 1.12 | tr | tr |
| NEOPHYTADIENE | tr | tr | tr | 0.56 | 1.16 | 1.13 | 0.33 |
| NEOPHYTADIENE ISOMER (T) | 0.11 | 0.19 | tr | 0.28 | 0.53 | 0.41 | 0.25 |
| METHYL PALMITATE | 0.81 | 1.50 | 0.23 | 0.69 | 1.67 | 0.86 | 1.27 |
| ISOPHYTOL | 3.86 | 5.91 | 1.02 | 9.60 | 10.15 | 5.41 | 6.88 |
| GERANYL LINALOOL | 1.05 | 1.31 | 0.21 | 4.08 | 4.72 | 1.96 | 1.80 |
| METHYL LINOLEATE | tr | tr | nd | 0.13 | 0.28 | 0.15 | 0.18 |
| METHYL LINOLENATE | 0.41 | 0.53 | tr | 1.39 | 2.46 | 1.23 | 3.27 |
| METHYL OLEATE | 0.16 | 0.27 | tr | 0.31 | 0.71 | 0.48 | 0.46 |
| (E)-PHYTOL | 0.96 | 1.19 | tr | 10.76 | 9.79 | 5.19 | 7.73 |
| METHYL STEARATE LINOLENIC ACID | tr | tr | nd | 3.44 | 0.55 | 1.77 | 1.31 |

TABLE 1-continued

| Compound | Microwave Extract 1% w/w GC | Microwave Extract 2% w/w GC | Microwave Extract 3% w/w GC | Commercial Jasmin Extract 1% w/w GC | Commercial Jasmin Extract 1% w/w GC | Commercial Jasmin Extract 3% w/w GC | Commercial Jasmin Extract 4% w/w GC |
|---|---|---|---|---|---|---|---|
| (E)-PHYTYL ACETATE | 0.91 | 1.67 | 0.24 | 7.91 | 6.25 | 4.30 | 3.73 |
| (E)-PHYTYL BENZOATE | nd | nd | nd | 0.76 | 0.71 | 0.45 | 0.47 |
| SQUALENE | tr | tr | nd | 3.41 | 6.30 | 3.74 | 3.52 |
| SQUALENE EPOXIDE | tr | tr | nd | 2.78 | 3.83 | 8.23 | 5.11 |

These data suggest that the methods disclosed herein are capable of reproducibly producing an essential oil from *Jasminium grandiflorum* comprising from 7 to 11% w/w (z)-jasmone, from 10 to 17% w/w (±)-3,7-Dimethyl-1,6-octadien-3-ol, from 40 to 62% w/w benzyl acetate, and from 1 to 7.1% w/w benzyl benzoate. By way of comparison, jasmine essential oils obtained from commercial sources comprised from 1.5 to 7% w/w (z)-jasmone, from 1.5 to 5% w/w (±)-3,7-Dimethyl-1,6-octadien-3-ol, from 6 to 17% w/w benzyl acetate, and from 6 to 13% w/w benzyl benzoate.

The three compositions comprising distillate collected from the microwave extractor, prior to application to the XAD4 resin column also smelled more like freshly isolated jasmine flowers than the essential oils from commercial sources.

Example 3

Extracting Essential Oils from *Cananga Odorata*

Freshly isolated flowers from *Cananga odorata* are introduced into a microwave extractor at a rate of 4 Kg per hour. The length of the microwave extractor is 2.5 m. The freshly isolated flowers are subjected to microwave energy at a power of 200 Watts, to obtain a distillate, while the temperature of the chamber within the microwave extractor (referring to FIGS. 1 and 2 for example), is maintained at a temperature between 60 and 80 degrees Celsius. The transit time of the plant biomass through the microwave extractor is approximately 20 minutes.

The distillate is collected at the bottom of the microwave extractor by gravimetry, and the distillate is applied to a XAD4 resin column. Once the resin in the column becomes saturated, materials bound to the resin column are desorbed, using ethanol, with a flow rate of approximately 5 bed volumes per hour, wherein the total volume is adjusted to result in a composition comprising essential oils having the desired concentration in ethanol. Here, approximately 3 to 15 bed volumes may be required to elute the essential oil off the resin column.

In some experiments, the distillate that may be collected from the microwave extractor, prior to application to the XAD4 resin column may comprise essential oils having a concentration from 200 to 3000 ppm. The composition of the essential oils will be analyzed by GC.

Example 4

Extracts Prepared from *Piper Nigrum* by a Method According to the Aspects Presented Herein Dried peppercorns of the *Piper nigrum* plant were ground, and introduced into a microwave extractor at a rate of 8 Kg per hour. The length of the microwave extractor was 2.5 m. The ground peppercorns were subjected to microwave energy at a power of 0.27 KWH per kilogram of biomass, to obtain a distillate, while the temperature of the chamber within the microwave extractor (referring to FIGS. 1 and 2 for example), was maintained at a temperature between 81 and 100 degrees Celsius. Steam was also added to the extractor at a rate of 8 Kg/hour. The transit time of the biomass through the microwave extractor was approximately 20 minutes.

The distillate was collected at the bottom of the microwave extractor by gravimetry, and the distillate was applied to a XAD4 resin column. Once the resin in the column became saturated, materials bound to the resin column were desorbed, using ethanol, with a flow rate of approximately 5 bed volumes per hour, wherein the total volume was adjusted to result in a composition comprising extracts having the desired concentration in ethanol. Here, approximately 3 to 15 bed volumes were required to elute the extract off the resin column. The composition of the ethanolic extract (Microwave Extract 1) and the distillate (Microwave Extract 2) was analyzed by GC, and the results are reported in Table 2 below.

TABLE 2

| Compound | Microwave Extract 1 % w/w GC | Microwave Extract 2 % w/w GC | Commercial Extract 1 % w/w GC | Commercial Extract 2 % w/w GC | Commercial Extract 3 % w/w GC |
|---|---|---|---|---|---|
| α-THUJENE | 1.67 | 0.77 | tr | 1.11 | tr |
| α-PINENE | 8.95 | 5.70 | tr | 5.99 | 0.68 |
| CAMPHENE | 0.17 | 0.14 | nd | 0.14 | tr |
| SABINENE | 14.31 | 9.43 | 0.69 | 6.67 | tr |
| β-PINENE | 15.75 | 12.41 | 0.64 | 9.19 | 2.28 |
| MYRCENE | 2.77 | 1.38 | 0.36 | 1.69 | 0.57 |
| α-PHELLANDRENE | 1.66 | tr | 0.31 | 2.17 | 0.41 |
| δ3-CARENE | 10.72 | 6.62 | 1.30 | 10.50 | 3.35 |
| α-TERPINENE | tr | tr | tr | 0.48 | tr |
| p-CYMENE | 0.73 | 1.16 | 0.16 | 0.75 | 0.54 |
| β-PHELLANDRENE | Coelut° (≈0.7%) | Coelut° (≈0.5%) | 0.61 | 1.52 | Coelut° |

TABLE 2-continued

| Compound | Microwave Extract 1 % w/w GC | Microwave Extract 2 % w/w GC | Commercial Extract 1 % w/w GC | Commercial Extract 2 % w/w GC | Commercial Extract 3 % w/w GC |
|---|---|---|---|---|---|
| LIMONENE | 27.91 | 20.56 | 6.84 | 15.29 | 7.97 |
| (E)-b-OCIMENE | 0.18 | tr | 0.11 | 0.12 | tr |
| γ-TERPINENE | 0.10 | tr | tr | 0.78 | tr |
| (E)-SABINENE HYDRATE | 0.16 | 0.23 | 0.28 | tr | tr |
| ISOSYLVETERPINOLENE | 0.12 | tr | tr | tr | tr |
| TERPINOLENE | 0.39 | tr | 0.28 | 0.61 | tr |
| (Z)-SABINENE HYDRATE | tr | 0.23 | 0.23 | tr | tr |
| LINALOOL | 0.11 | 0.23 | 0.24 | 0.44 | tr |
| 4-TERPINEOL | 0.15 | 0.71 | 0.36 | 0.98 | 0.15 |
| α-TERPINEOL | tr | 0.28 | 0.29 | tr | tr |
| 2-METHYL-5-(2-PROPANYL)-3-CYCLOHEXENE-1,2-DIOL ISOMER | tr | 0.50 | tr | tr | tr |
| δ-ELEMENE | 0.62 | 0.60 | 3.78 | 2.16 | 1.42 |
| α-CUBEBENE | 0.10 | 0.15 | 0.18 | 0.24 | tr |
| α-COPAENE | 0.17 | 0.31 | 0.37 | 2.41 | tr |
| β-ELEMENE | 0.32 | 0.63 | 1.15 | 1.18 | 1.10 |
| α-GURJUNENE | 0.11 | 0.15 | 0.27 | 0.18 | tr |
| β-CARYOPHYLLENE | 7.64 | 11.58 | 22.23 | 22.31 | 32.38 |
| α-GUAIENE | 0.25 | 0.43 | 0.70 | 0.28 | 0.57 |
| α-HUMULENE | 0.48 | 1.02 | 1.64 | 1.48 | 1.90 |
| GERMACRENE D | 0.22 | 0.14 | 1.16 | 0.50 | 1.67 |
| β-SELINENE | 0.90 | 2.74 | 3.43 | 1.45 | 1.42 |
| α-SELINENE | 0.81 | 1.51 | 3.45 | 1.16 | 1.06 |
| β-BISABOLENE | tr | tr | tr | 0.86 | tr |
| δ-CADINENE | tr | tr | tr | 0.87 | tr |
| ELEMOL | tr | tr | tr | 0.45 | tr |
| SPATHULENOL | 0.15 | 1.53 | 0.90 | tr | tr |
| CARYOPHYLLENE OXIDE (2 ISOMERES) | 0.31 | 5.26 | 0.92 | 0.61 | 1.45 |
| HUMULENE OXIDE | tr | 0.38 | 0.12 | tr | tr |
| ISOSPATHULENOL | 0.26 | 1.40 | 1.24 | 0.14 | 1.20 |
| PELLITORIN | nd | nd | 0.94 | nd | 2.67 |
| PALMITIC ACID | nd | nd | 0.35 | nd | 0.15 |
| 1-CINNAMOYL PIPERIDINE | nd | nd | 0.31 | nd | 0.10 |
| SARMENTINE (=1-(1-PYRROLIDINYL)-(E,E)-2,4-DECADIEN-1-ONE) | nd | nd | 0.23 | nd | 0.23 |
| PHYTOL | nd | nd | 0.22 | nd | nd |
| NEOPELLITORIN B | nd | nd | 0.24 | nd | 0.22 |
| LINOLEIC ACID | nd | nd | 1.28 | nd | 0.55 |
| N-ISOBUTYL-DODECA-2,4-DIENAMIDE | nd | nd | | nd | |
| OLEIC ACID | nd | nd | 0.26 | nd | tr |
| 1-DODECANOYL PIPERIDINE | nd | nd | 0.20 | nd | tr |
| N-(2,4-DODECADIENOYL) PYRROLIDINE | nd | nd | 0.32 | nd | 0.17 |
| N-(4',4'-DIHYDROPIPEROYL) PIPERIDINE | nd | nd | 1.54 | nd | 1.86 |
| AMIDE MW = 335G/MOL (T) | nd | nd | 0.77 | nd | 1.63 |
| AMIDE MW = 333G/MOL (T) | nd | nd | 3.16 | nd | 0.63 |
| AMIDE MW = 335G/MOL (T) | nd | nd | 1.57 | nd | 0.33 |
| PIPERINE | nd | nd | 3.57 | nd | 3.20 |
| PIPERINE DERIV. MW = 315G/MOL (T) | nd | nd | 2.21 | nd | 1.09 |
| AMIDE MW = 329G/MOL (T) | nd | nd | 0.87 | nd | 0.67 |
| PIPERIDINE DERIV. MW = 343G/MOL (T) | nd | nd | 3.89 | nd | 3.39 |

These data suggest that the methods disclosed herein are capable of reproducibly producing an essential oil from *Piper nigrum* comprising from 9 to 15% w/w sabinine, from 12 to 16% w/w β-pinene, from 6 to 11% w/w δ3-carene, and from 20 to 30% w/w limonene. Furthermore, amount of beta-caryophyllene in an essential oil from *Piper nigrum* produced using the methods disclosed herein was from 7 to 12% w/w, and piperine was not detected.

By way of comparison, an essential oil from *Piper nigrum* obtained from a commercial source comprised approximately 3% w/w piperine, from 20 to 35% w/w beta-caryophyllene, from 0.5 to 7% w/w sabinine, from 0.5 to 10% w/w β-pinene, from 1 to 11% w/w δ3-carene, and from 6 to 16% w/w limonene.

Example 5

Extracts Prepared from Pears by a Method According to the Aspects Presented Herein Fresh pear fruits were sliced, and introduced into a microwave extractor at a rate of 7 Kg per hour. The length of the microwave extractor was 2.5 m. The sliced pears were subjected to 200 W microwave energy at a power of 0.33 KWH per kilogram of biomass, to obtain a distillate, while the temperature of the chamber within the microwave extractor (referring to FIGS. 1 and 2 for example), was maintained at a temperature between 60 and 80 degrees Celsius. The transit time of the biomass through the microwave extractor was approximately 20 minutes.

The distillate was collected at the bottom of the microwave extractor by gravimetry, and the distillate was applied to a XAD4 resin column. Once the resin in the column became saturated, materials bound to the resin column were desorbed, using ethanol, with a flow rate of approximately 5 bed volumes per hour, wherein the total volume was adjusted to result in a composition comprising extract having the desired concentration in ethanol. Here, approximately 3 to 15 bed volumes were required to elute the extract off the resin column. The composition of the ethanolic extract (Microwave Extract 1) and the distillate (Microwave Extract 2) was analyzed by GC, and the results are reported in Table 3 below.

TABLE 3

| Compound | Microwave Extract 1 % w/w GC | Microwave Extract 2 % w/w GC | Commercial Extract % w/w GC |
|---|---|---|---|
| 1-PROPANOL | 2.2 | 0.1 | 16.7 |
| BUTYL ACETATE | 11.0 | 0.3 | 2.2 |
| HEXANAL | nd | nd | 1.3 |
| ISOBUTYL ALCOHOL | 1.4 | 0.0 | 8.7 |
| 1-BUTANOL | 23.4 | 0.7 | 33.1 |
| PENTYL ACETATE | 0.3 | nd | nd |
| (E)-2-HEXENAL | nd | nd | 3.4 |
| 2-METHYLBUTYL ALCOHOL | 0.6 | nd | 6.7 |
| 3-METHYLBUTYL ALCOHOL | nd | nd | 3.7 |
| 1-PENTANOL | 0.1 | nd | 0.6 |
| HEXYL ACETATE | 6.2 | 0.1 | nd |
| ACETOIN (=ACETYLMETHYL CARBINOL) | 1.5 | nd | 2.2 |
| ACETOL | 0.9 | 3.2 | nd |
| 1-HEXANOL | 2.5 | 0.1 | 13.3 |
| (Z)-3-HEXENOL | nd | nd | 0.4 |

TABLE 3-continued

| Compound | Microwave Extract 1 % w/w GC | Microwave Extract 2 % w/w GC | Commercial Extract % w/w GC |
|---|---|---|---|
| 1-HYDROXY-3-BUTEN-2-ONE | 0.6 | nd | nd |
| 2-OXO-3-BUTENOL (T) | nd | 3.1 | nd |
| (E)-2-HEXENOL | nd | nd | 2.5 |
| ACETIC ACID | 2.1 | 7.5 | nd |
| FURFURAL | 1.5 | 0.6 | 0.4 |
| 2-ETHYL-1-HEXANOL | 0.3 | nd | nd |
| BENZALDEHYDE | nd | nd | 0.2 |
| 4-CYCLOPENTENE-1,3-DIONE | nd | 0.2 | nd |
| 3-(METHYLTHIO)PROPYL ACETATE | 0.1 | nd | nd |
| FURFURYL ALCOHOL | 0.6 | 1.4 | nd |
| 2-METHYLBUTYRIC ACID | 1.4 | 0.4 | nd |
| 3-(METHYLTHIO)PROPYL ALCOHOL | 0.2 | nd | nd |
| CRATONE (=2(5H)-FURANONE) | nd | 0.3 | nd |
| 2-HYDROXY-2-CYCLOPENTENONE | nd | 1.5 | nd |
| CITRONELLOL | 1.3 | nd | nd |
| METHYL 2,4-DECADIENOATE | 0.9 | nd | nd |
| NEROL | 0.5 | nd | nd |
| ETHYL 2,4-DECADIENOATE | 0.7 | nd | nd |
| QUINCESTER (=ETHYL (E,Z,Z)-2,4,7-DECATRIENOATE) | 0.1 | nd | nd |
| GERANIOL | 1.6 | nd | nd |
| METHYL 3-HYDROXYOCTANOATE | 1.3 | nd | 0.1 |
| HEXANOIC ACID | nd | 0.9 | nd |
| ETHYL 3-HYDROXYOCTANOATE | 3.7 | 0.1 | 0.3 |
| 2-PHENYLETHYL ALCOHOL | 1.4 | nd | nd |
| METHYL (Z)-3-HYDROXY-5-OCTENOATE | 0.1 | nd | nd |
| ETHYL (Z)-3-HYDROXY-5-OCTENOATE | 0.2 | nd | nd |
| 1,3-DIHYDROXYACETONE ISOMER (T) | 6.1 | 45.6 | nd |
| 1,3-OCTANEDIOL | 6.8 | 0.3 | nd |
| P-VINYL GUAIACOL | 0.1 | nd | nd |
| DIHYDROMYRCENOL | 0.2 | nd | nd |
| 5-HYDROXY-5,6-DIHYDROMALTOL | 0.8 | 3.6 | nd |
| P-VINYL PHENOL | 0.4 | nd | nd |
| 5-HYDROXYMETHYL FURFURAL | 1.2 | 4.7 | nd |
| 5-HYDROXYMETHYL FURFUROL | 0.1 | 1.3 | nd |

These data suggest that the methods disclosed herein are capable of reproducibly producing an extract from pears comprising from 0.2 to 12% w/w butyl acetate, from 0.1 to 6% w/w hexyl acetate, from 3 to 15% w/w acetol, from 2 to 8% w/w acetic acid, from 0.5 to 2% w/w furfural, from 0.5 to 2% w/w furfural alcohol, from 0.2 to 2% w/w 2-methylbutyric acid, from 0.1 to 4% w/w ethyl 3-hydroxyoctanoate, from 6 to 46% w/w 1,3-dihydroxyacetone, from 0.2 to 7% w/w 1,3-octanediol, from 0.5 to 4% w/w 5-hydroxy-5,6-dihydrolmaltol, and from 1 to 4% w/w 5-hydroxymethyl furfural. In addition, in the ethanolic extract, methyl 2,4- decadienoate, ethyl 2,4-decadienoate, geraniol, methyl 3-hydroxyoctanoate, 2-phenylethyl alcohol, and p-vinyl phenol were also present.

By way of comparison, a pear extract obtained from a commercial source comprised approximately 2% w/w butyl acetate, approximately 0.4% w/w furfural, and approximately 0.3% w/w ethyl 3-hydroxyoctanoate. In addition, hexyl acetate, acetol, acetic acid, furfural alcohol, 2-methylbutyric acid, 1,3-dihydroxyacetone, 1,3-octanediol, methyl 2,4-decadienoate, ethyl 2,4-decadienoate, 5-hydroxy-5,6-dihydrolmaltol, geraniol, methyl 3-hydroxyoctanoate, 2-phenylethyl alcohol, 5-hydroxymethyl furfural and p-vinyl phenol were not detected.

The extract from pears produced according to the methods described herein was very fruity and had a juicy, delicious and gourmand note of William pear and was very much powerful than the commercial extract.

Example 6

Extracts Prepared from Green Tea Leaves by a Method According to the Aspects Presented Herein Dried green tea leaves were hydrated by the addition of water to result in a biomass having a weight of 200% of the dried biomass, and introduced into a microwave extractor at a rate of 10 Kg per hour. The length of the microwave extractor was 2.5 m. The hydrated leaves were subjected to 300 W microwave energy at a power of 0.43 KWH per kilogram of biomass, to obtain a distillate, while the temperature of the chamber within the microwave extractor (referring to FIGS. 1 and 2 for example), was maintained at a temperature between 70 and 90 degrees Celsius. The transit time of the biomass through the microwave extractor was approximately 20 minutes.

The distillate was collected at the bottom of the microwave extractor by gravimetry, and the distillate was applied to a XAD4 resin column. Once the resin in the column became saturated, materials bound to the resin column were desorbed, using ethanol, with a flow rate of approximately 5 bed volumes per hour, wherein the total volume was adjusted to result in a composition comprising an extract having the desired concentration in ethanol. Here, approximately 3 to 15 bed volumes were required to elute the essential oil of the resin column. The composition of the ethanolic extract (Microwave Extract 1) and the distillate (Microwave Extract 2) was analyzed by GC, and the results are reported in Table 4 below.

TABLE 4

| Compound | Microwave Extract 1 % w/w GC | Microwave Extract 2 % w/w GC | Commercial Extract % w/w GC |
| --- | --- | --- | --- |
| 1-PENTEN-3-OL | 11.7 | 1.1 | 0.9 |
| 3-METHYLBUTYL ALCOHOL | 2.5 | 0.4 | 0.8 |
| ACETYLMETHYL CARBINOL (=3-HYDROXY-2-BUTANONE) | 1.0 | nd | 1.1 |
| ACETOL (=-HYDROXY-2-PROPANONE) | 1.1 | 2.7 | 14.8 |
| (Z)-2-PENTENOL | 6.9 | 1.0 | 0.5 |
| (Z)-3-HEXENOL | 2.8 | nd | nd |
| (Z)-LINALOOL OXIDE (FURANOID) | 0.8 | nd | nd |
| ACETIC ACID | 1.0 | 16.0 | 33.7 |

TABLE 4-continued

| Compound | Microwave Extract 1 % w/w GC | Microwave Extract 2 % w/w GC | Commercial Extract % w/w GC |
| --- | --- | --- | --- |
| (E)-LINALOOL OXIDE (FURANOID) | 1.4 | 0.2 | nd |
| BENZALDEHYDE | 1.0 | nd | nd |
| 3,5-OCTADIEN-2-ONE ISOMER (T) | 1.0 | nd | nd |
| LINALOOL | 4.1 | 0.5 | 1.6 |
| 3,5-OCTADIEN-2-ONE ISOMER (T) | 0.9 | nd | nd |
| 2-HYDROXY-2,6,6-TRIMETHYL-1-CYCLOHEXONE | 3.2 | nd | nd |
| FURFURYL ALCOHOL | 1.2 | nd | 8.2 |
| GERANIOL | 5.0 | 0.4 | 1.4 |
| BENZYL ALCOHOL | 5.0 | 1.0 | 1.3 |
| 2-PHENYLETHYL ALCOHOL | 3.5 | 0.7 | 1.6 |
| b-IONONE | 0.8 | nd | nd |
| 2-ACETYL PYRROLE | 2.7 | 0.7 | 3.7 |
| 4,5-EPOXY-b-IONONE | 0.8 | nd | nd |
| PHENOL | 1.4 | 0.6 | 1.0 |
| (Z)-JASMONE | 0.6 | nd | nd |
| DIHYDROACTINIDIOLIDE (=CASSIA LACTONE) | 1.3 | 2.3 | 2.1 |
| 4-VINYL PHENOL | 0.8 | 0.7 | 2.8 |
| CAFFEINE | 12.2 | 28.6 | 1.9 |

These data suggest that the methods disclosed herein are capable of reproducibly producing an extract from green tea leaves comprising from 12 to 30% w/w caffeine, and approximately 1% w/w furfuryl alcohol. In addition, 3,5-octadien-2-one, β-ionone, and 4,5-epoxy-β-ionone were also present.

By way of comparison, a green tea extract from a commercial source comprised approximately 2% w/w caffeine, and approximately 8% w/w furfural alcohol. In addition, 3,5-octadien-2-one, β-ionone, and 4,5-epoxy-β-ionone were absent.

Example 7

Extracts Prepared from Ginger Roots by a Method According to the Aspects Presented Herein Fresh ginger roots were sliced, and introduced into a microwave extractor at a rate of 7 Kg per hour. The length of the microwave extractor was 2.5 m. The sliced roots were subjected to 300 W microwave energy at a power of 0.45 KWH per kilogram of biomass, to obtain a distillate, while the temperature of the chamber within the microwave extractor (referring to FIGS. 1 and 2 for example), was maintained at a temperature between 70 and 90 degrees Celsius. The transit time of the biomass through the microwave extractor was approximately 20 minutes.

The distillate was collected at the bottom of the microwave extractor by gravimetry, and the distillate was applied to a XAD4 resin column. Once the resin in the column became saturated, materials bound to the resin column were desorbed, using ethanol, with a flow rate of approximately 5 bed volumes per hour, wherein the total volume was adjusted to result in a composition comprising an extract having the desired concentration in ethanol. Here, approximately 3 to 15 bed volumes were required to elute the essential oil of the resin column. The composition of the ethanolic extract (Microwave Extract 1) and the distillate (Microwave Extract 2) was analyzed by GC, and the results are reported in Table 5 below.

TABLE 5

| Compound | Microwave Extract 1 % w/w GC | Microwave Extract 2 % w/w GC | Commercial Extract % w/w GC |
|---|---|---|---|
| α-PINENE | nd | nd | 1.5 |
| 2-METHYL-3-BUTEN-2-OL | 0.2 | nd | <0.1 |
| CAMPHENE | 0.0 | nd | 4.5 |
| β-PINENE | nd | nd | 0.2 |
| HEXANAL | 0.1 | nd | <0.1 |
| α-PHELLANDRENE | nd | nd | 0.2 |
| MYRCENE | nd | nd | 1.0 |
| 2-HEPTANONE | 0.4 | nd | <0.1 |
| LIMONENE | nd | nd | 1.0 |
| β-PHELLANDRENE | nd | nd | 4.4 |
| EUCALYPTOL | 14.8 | 13.9 | 2.9 |
| TERPINOLENE | nd | nd | 0.2 |
| OCTANAL | 0.0 | nd | <0.1 |
| 2-HEPTANOL | 5.7 | 6.6 | 0.6 |
| 6-METHYL-5-HEPTEN-2-ONE | 2.1 | nd | 0.3 |
| 2-NONANONE | 0.3 | nd | 0.2 |
| (E)-2-OCTENAL | 0.1 | nd | <0.1 |
| CITRONELLAL | 0.6 | 0.3 | 0.6 |
| α-COPAENE | nd | nd | 0.3 |
| CAMPHOR | 0.3 | nd | <0.1 |
| 2-NONANOL | 0.9 | 0.7 | 0.4 |
| (Z)-ISOCITRAL | 0.3 | nd | <0.1 |
| LINALOOL | 2.2 | 2.0 | 0.6 |
| (E)-ISOCITRAL | 0.6 | nd | <0.1 |
| β-ELEMENE | nd | nd | 0.4 |
| 2-UNDECANONE | nd | nd | 0.7 |
| 4-TERPINEOL | 0.6 | 0.6 | 0.2 |
| OXYGENATED TERPENE MW = 152G/MOL (T) | 0.5 | nd | <0.1 |
| NERAL | 19.7 | 25.0 | 8.8 |
| α-TERPINEOL | 3.7 | 3.5 | 0.9 |
| BORNEOL | 3.7 | 3.7 | 1.8 |
| γ-CADINENE | nd | nd | 2.0 |
| ZINGIBERENE | nd | nd | 18.5 |
| GERANIAL | 26.1 | 29.0 | 16.3 |
| OXYGENATED TERPENE MW = 152G/MOL (T) | 0.9 | nd | <0.1 |
| (E,E)-α-FARNESENE | nd | nd | 5.4 |
| β-SESQUIPHELLANDRENE | nd | nd | 6.9 |
| AR-CURCUMENE | nd | nd | 3.3 |
| CITRONELLOL | 2.3 | 2.0 | 3.3 |
| MYRTENOL | 0.2 | nd | <0.1 |
| NEROL | 0.7 | 0.7 | 0.2 |
| GERMACRENE B | nd | nd | 0.5 |
| TERPINOLEN-6-OL (T) | 0.5 | nd | <0.1 |
| GERANIOL | 3.0 | 3.0 | 1.0 |
| (E)-NEROLIDOL | nd | nd | 0.5 |
| ELEMOL | nd | nd | 0.3 |
| ZINGIBERENOL | nd | nd | 0.6 |
| (E)-SESQUIPIPERITOL | nd | nd | 0.4 |

These data suggest that the methods disclosed herein are capable of reproducibly producing an essential oil from ginger roots comprising from 13 to 15% w/w eucalyptol, from 2 to 6% w/w 6-methyl-5-hepten-2-one, from 19 to 25% w/w neral, approximately 0.4% w/w 2-heptanone, from 26 to 29% w/w geranial, approximately 0.7% w/w nerol, and approximately 0.3% w/w geraniol. Furthermore, zingiberene was not detected.

By way of comparison, an ginger essential oil obtained from a commercial source comprised approximately 0.1% w/w 2-heptanone, approximately 2.9% w/w eucalyptol, approximately 0.3% w/w 6-methyl-5-hepten-2-one, approximately 8.8% w/w neral, approximately 16.3% w/w geranial, approximately 18.5% w/w zingiberene, approximately 0.2% w/w nerol, and approximately 1% w/w geraniol.

Example 8

Extracts Prepared from Coffee Beans by a Method According to the Aspects Presented Herein Freshly roasted coffee beans were ground, and introduced into a microwave extractor at a rate of 12 Kg per hour. The length of the microwave extractor was 2.5 m. The ground beans were subjected to 120 W microwave energy at a power of 0.24 KWH per kilogram of biomass, to obtain a distillate, while the temperature of the chamber within the microwave extractor (referring to FIGS. 1 and 2 for example), was maintained at a temperature between 70 and 90 degrees Celsius. The transit time of the biomass through the microwave extractor was approximately 20 minutes.

The distillate was collected at the bottom of the microwave extractor by gravimetry, and the distillate was applied to a XAD4 resin column. Once the resin in the column became saturated, materials bound to the resin column were desorbed, using ethanol, with a flow rate of approximately 5 bed volumes per hour, wherein the total volume was adjusted to result in a composition comprising essential oils having the desired concentration in ethanol. Here, approximately 3 to 15 bed volumes were required to elute the essential oil of the resin column. The composition of the ethanolic extract (Microwave Extract 1) and the distillate (Microwave Extract 2) was analyzed by GC, and the results are reported in Table 6 below.

TABLE 6

| Compound | Microwave Extract 1 % w/w GC | Microwave Extract 2 % w/w GC | Commercial Extract % w/w GC |
|---|---|---|---|
| 2,3-PENTANEDIONE | 0.6 | 0.6 | nd |
| CYCLOPENTANONE | 0.1 | nd | nd |
| PYRIDINE | 2.3 | 6.7 | 0.4 |
| PYRAZINE | 0.6 | 0.6 | nd |
| 2-FURFURYL METHYL ETHER | 0.1 | nd | nd |
| ISOPRENOL | 0.2 | nd | nd |
| COFFEE FURANONE (=2-METHYLTETRAHYDROFURAN-3-ONE) | 2.3 | 2.0 | 0.1 |
| 2-METHYL PYRAZINE | 3.7 | 3.1 | 0.6 |
| ACETYLMETHYL CARBINOL | 0.7 | 1.7 | nd |
| ACETOL | 0.7 | 7.5 | 0.0 |
| 2,5-DIMETHYL PYRAZINE | 1.1 | 1.1 | 1.2 |
| 2,6-DIMETHYL PYRAZINE | 1.3 | 1.1 | |
| 2-ETHYL PYRAZINE | 0.6 | 0.5 | 0.2 |
| 3-HYDROXY-2-PENTANONE | 0.5 | 0.5 | nd |
| 2,3-DIMETHYL PYRAZINE | 0.2 | 0.2 | 0.1 |
| 2-CYCLOPENTENONE | 0.2 | 0.2 | nd |
| 2-HYDROXY-3-PENTANONE | 0.4 | 0.4 | nd |
| 1-HYDROXY-2-BUTANONE | 0.8 | 1.2 | nd |
| DIACETONE ALCOHOL | nd | nd | nd |
| 2-ETHYL-6-METHYL PYRAZINE | 0.4 | 0.4 | 1.6 |
| 2-ETHYL-5-METHYL PYRAZINE | 0.2 | 0.3 | 0.5 |
| 2-ETHYL-3-METHYL PYRAZINE | 0.4 | 0.1 | 0.3 |
| 3-ETHYL-2,5-DIMETHYL PYRAZINE | nd | nd | nd |
| ACETIC ACID | 5.3 | 5.2 | 10.9 |
| FURFURAL | 3.5 | 4.7 | 0.4 |
| 2-OXOPROPYL ACETATE | 3.5 | 3.2 | nd |
| FURFURYL METHYL SULFIDE | nd | nd | nd |
| FURFURYL FORMATE | 1.5 | 1.4 | 0.1 |
| 2-ACETYL FURAN | | | 0.3 |
| PYRROLE | 0.2 | 0.2 | nd |
| (2-FURYL)-2-PROPANONE | 0.2 | 0.2 | nd |
| 2-OXOPROPYL PROPANOATE | 0.5 | 0.4 | 0.3 |
| 2-OXOBUTYL ACETATE | 0.5 | 2.1 | nd |
| FURFURYL ACETATE | 1.5 | | 2.1 |
| PROPANOIC ACID | 2.5 | 0.9 | 0.8 |
| 5-METHYL FURFURAL | 2.7 | 2.5 | 2.0 |

TABLE 6-continued

| Compound | Microwave Extract 1 % w/w GC | Microwave Extract 2 % w/w GC | Commercial Extract % w/w GC |
|---|---|---|---|
| 2-FORMYL-5-METHYL PYRROLE | 3.7 | 0.3 | 0.3 |
| g-BUTYROLACTONE | | 3.2 | 3.3 |
| 2-ACETYL-1-METHYL PYRROLE | 0.2 | 0.2 | 0.3 |
| FURFURYL ALCOHOL | 42.3 | 36.6 | 24.3 |
| ISOVALERIC ACID | 2.8 | 1.5 | 1.8 |
| N-FURFURYL PYRROLE | nd | nd | 0.5 |
| NUSSOL (=2-HYDROXY-3-METHYL-2-CYCLOPENTEN-1-ONE) | 0.4 | 0.3 | 1.2 |
| GUAIACOL (=2-METHOXYPHENOL) | 0.3 | 0.2 | 1.4 |
| ETHYL CYCLOPENTENOLONE | 0.1 | 0.1 | nd |
| 2-ACETYL PYRROLE | 0.5 | 0.4 | 2.6 |
| DIFURFURYL ETHER | 0.1 | 0.1 | 0.6 |
| PHENOL | 0.3 | 0.4 | 0.7 |
| 2-FORMYL PYRROLE | 0.5 | 0.4 | Coelut° |
| 2-FORMYL-5-METHYLPYRROLE | 0.1 | 0.1 | nd |
| CAPROLACTAM | 0.1 | 0.1 | nd |
| 4-VINYL GUAIACOL | 0.2 | nd | 3.2 |

These data suggest that the methods disclosed herein are capable of reproducibly producing an extract from coffee beans comprising approximately 0.6% w/w 2,3-pentanedione, from 2 to 2.5% w/w coffee furanone, from 3 to 4% w/w 2-methyl pyrazine, from 0.5 to 2% w/w acetylmethyl carbinol, from 0.5 to 8% w/w acetol, approximately 0.2% w/w 2-cyclopentenone, approximately 0.4% w/w 2-hydroxy-3-pentanone, 0.5 to 1.5% w/w 1-hydroxy-2-butanone, 3 to 5% w/w furfural, approximately 1.5% w/w furfuryl formate, 0.5 to 3% w/w propanoic acid, and 35 to 45% w/w furfuryl alcohol.

By way of comparison, extracts from commercial sources comprised 0.1% w/w coffee furanone, 0.6% w/w 2-methyl pyrazine, 0.4% w/w furfural, 0.1% w/w furfuryl formate, 0.8% w/w propanoic acid, 24% w/w furfuryl alcohol. Furthermore, 2,3-pentanedione, acetylmethyl carbinol, acetol, 2-cyclopentenone, 2-hydroxy-3-pentanone, and 1-hydroxy-2-butanone were not detected.

The differences in the coffee extract obtained according to a method according to the aspects presented herein differs from a commercially obtained extract in volatile compounds that contribute to the sweet notes and olfactive profile of fresh coffee.

Publications cited throughout this document are hereby incorporated by reference in their entirety. Although the various aspects of the invention have been illustrated above by reference to examples and preferred embodiments, it will be appreciated that the scope of the invention is defined not by the foregoing description but by the following claims properly construed under principles of patent law.

The invention claimed is:

1. A method,
   wherein the method obtains an extract from plant biomass,
   wherein the extract is an essential oil,
   wherein the method comprises the steps of:
   a. obtaining the plant biomass;
   b. placing the plant biomass onto a conveyor belt, having a length, and introducing the plant biomass into a vessel having a length, via the conveyor belt,
      wherein the plant biomass is introduced into the vessel by moving the conveyer belt at a first velocity,
      wherein the plant biomass is introduced into the vessel at a rate; and
      wherein the temperature of the inside of the vessel is from 40 to 100 degrees Celsius;
   c. subjecting the plant biomass to microwave energy, of a first intensity, for a time sufficient to heat the plant biomass to a temperature to vaporize water within the plant biomass, thereby producing a distillate, wherein the first intensity of the microwave energy is from 0.2 KWH/Kg biomass to 0.6 KWH/Kg biomass, wherein the temperature of the inside of the vessel is maintained between 40 and 100 degrees Celsius; and
   d. collecting the distillate.

2. The method of claim 1, wherein the time sufficient to heat the plant biomass to the temperature to vaporize water is controlled by the first velocity of the conveyer belt, the length of the conveyer belt, the first intensity of the microwave energy, the length of the vessel, the temperature within the vessel, or any combination thereof.

3. The method of claim 1, wherein the plant biomass is introduced into the vessel at a rate of at least 4 Kg of plant biomass per hour.

4. The method of claim 1, wherein the first intensity of the microwave energy is from 100 to 3000 Watts.

5. The method of claim 1, wherein the temperature of the inside of the vessel is from 40 to 90 degrees Celsius.

6. The method of claim 1, wherein the collected distillate comprises from 200 to 3000 ppm essential oils.

7. The method of claim 1, wherein the collected distillate is further processed to obtain the essential oils.

* * * * *